(12) United States Patent
Sheahan et al.

(10) Patent No.: US 10,111,749 B2
(45) Date of Patent: *Oct. 30, 2018

(54) PROSTHETIC VALVE WITH FLOW DIRECTOR

(71) Applicant: Medtronic Vascular, Inc., Santa Rosa, CA (US)

(72) Inventors: Edmond Sheahan, Ballybrit (IE); Niall Duffy, Ballybrit (IE)

(73) Assignee: Medtronic Vascular, Inc., Santa Rosa, CA (US)

( * ) Notice: Subject to any disclaimer, the term of this patent is extended or adjusted under 35 U.S.C. 154(b) by 98 days.

This patent is subject to a terminal disclaimer.

(21) Appl. No.: 14/989,839

(22) Filed: Jan. 7, 2016

(65) Prior Publication Data

US 2016/0113764 A1    Apr. 28, 2016

Related U.S. Application Data

(63) Continuation-in-part of application No. 14/301,632, filed on Jun. 11, 2014, now Pat. No. 9,662,203.

(51) Int. Cl.
*A61F 2/24* (2006.01)
*A61F 2/06* (2013.01)

(52) U.S. Cl.
CPC .......... *A61F 2/2418* (2013.01); *A61F 2/2412* (2013.01); *A61F 2002/068* (2013.01)

(58) Field of Classification Search
CPC ............. A61F 2002/068; A61F 2/2418; A61F 2002/061; A61F 2002/067; A61F 2002/075; A61F 2220/0008; A61F 2220/0016; A61F 2/01; A61F 2/06; A61F 2/07;

(Continued)

(56) References Cited

U.S. PATENT DOCUMENTS

| 8,257,434 B2 | 9/2012 | Matheny |
| 8,562,673 B2 | 10/2013 | Yeung et al. |
| 9,681,967 B2 * | 6/2017 | Kassab ............. A61F 2/90 |

(Continued)

FOREIGN PATENT DOCUMENTS

| GB | 2371988 | 8/2002 | |
| WO | WO 0238085 A1 * | 5/2002 | ............ A61F 2/90 |
| WO | WO 2017040366 A1 * | 3/2017 | ............ A61F 2/06 |

OTHER PUBLICATIONS

Querzoli et al., "Effect of the Prosthetic Mitral Valve on Vortex Dynamics and Turbulence of the Left Ventricular Flow" Physics of Fluid 22, Apr. 19, 2001 (2010).

(Continued)

*Primary Examiner* — Seema Mathew

(74) *Attorney, Agent, or Firm* — Dicke, Billig & Czaja, PLLC

(57) ABSTRACT

A prosthetic valve comprising a stent frame, a valve structure, and a baffle structure. The stent frame defines a lumen. The valve structure is disposed within the lumen, and defines an inflow side and an outflow side. An outflow track is established within the lumen downstream of the outflow side and along which fluid flow from the valve structure progresses. The baffle structure is connected to the stent frame downstream of the outflow side. In some embodiments, the baffle structure directs blood flow into designated areas to encourage laminar flow and eliminate or reduce turbulence.

19 Claims, 11 Drawing Sheets

(58) Field of Classification Search
CPC .. A61F 2/2475; A61F 2/89; A61F 2/90; A61F 2/24; A61F 2/2412
See application file for complete search history.

(56) References Cited

U.S. PATENT DOCUMENTS

| | | | | |
|---|---|---|---|---|
| 9,844,452 | B2* | 12/2017 | Furey | A61F 2/82 |
| 9,872,759 | B2* | 1/2018 | Kassab | A61F 2/06 |
| 2006/0184194 | A1* | 8/2006 | Pal | A61F 2/013 |
| | | | | 606/200 |
| 2006/0259128 | A1 | 11/2006 | Pavcnik | |
| 2007/0043431 | A1 | 2/2007 | Melsheimer | |
| 2008/0140110 | A1* | 6/2008 | Spence | A61F 2/06 |
| | | | | 606/200 |
| 2009/0177270 | A1* | 7/2009 | Agnew | A61F 2/2418 |
| | | | | 623/1.24 |
| 2010/0106180 | A1* | 4/2010 | Strother | A61F 2/82 |
| | | | | 606/200 |
| 2012/0101572 | A1* | 4/2012 | Kovalsky | A61F 2/2418 |
| | | | | 623/2.19 |
| 2013/0274855 | A1 | 10/2013 | Stante | |
| 2013/0282113 | A1 | 10/2013 | Punga | |
| 2014/0046433 | A1 | 2/2014 | Kovalsky | |
| 2014/0088692 | A1* | 3/2014 | Wright | A61F 2/2418 |
| | | | | 623/2.11 |
| 2014/0343664 | A1* | 11/2014 | Furey | A61F 2/06 |
| | | | | 623/1.18 |
| 2015/0148896 | A1* | 5/2015 | Karapetian | A61F 2/246 |
| | | | | 623/2.11 |
| 2015/0359631 | A1 | 12/2015 | Sheahan et al. | |
| 2017/0086959 | A1* | 3/2017 | Verin | A61F 2/01 |
| 2018/0078394 | A1* | 3/2018 | Zimmerman | A61F 2/966 |
| 2018/0147045 | A1* | 5/2018 | Kassab | A61F 2/2475 |

OTHER PUBLICATIONS

Pedrizzetti et al., "On the Left Ventricular Vortex Reversal After Mitral Valve Replacement" Annals of Biomedical Engineering, vol. 38, No. 3, Mar. 2010, pp. 769-773.
PCT/US2017/012429 The International Search Report and The Written Opinion of the International Searching Authority, dated Mar. 17, 2017.

* cited by examiner

PROSTHETIC VALVE WITH FLOW DIRECTOR

CROSS-REFERENCE TO RELATED APPLICATIONS

This application is a continuation-in-part of U.S. application Ser. No. 14/301,632, filed Jun. 11, 2014, and entitled "Prosthetic Valve With Vortices-Including Baffle"; the entire teachings of which are incorporated herein by reference.

BACKGROUND

The present disclosure relates to prosthetic valves. More particularly, it relates structures, devices and methods for manipulating fluid flow at a prosthetic valve, such as a prosthetic heart valve.

A human heart includes four heart valves that determine the pathway of blood flow through the heart: the mitral valve, the tricuspid valve, the aortic valve, and the pulmonary valve. The mitral and tricuspid valves are atrio-ventricular valves, which are between the atria and the ventricles, while the aortic and pulmonary valves are semilunar valves, which are in the arteries leaving the heart. The tricuspid valve, also known as the right atrio-ventricular valve, is a tri-flap valve located between the right atrium and the right ventricle. The mitral valve, also known as the bicuspid or left atrio-ventricular valve, is a dual-flap valve located between the left atrium and the left ventricle.

As with other valves of the heart, the mitral valve is a passive structure in that it does not itself expend any energy and does not perform any active contractile function. The mitral valve includes an annulus that provides attachment for the two leaflets (anterior leaflet and posterior leaflet) that each open and close in response to differential pressures on either side of the valve. The leaflets of the mitral valve are dissimilarly shaped. The anterior leaflet is more firmly attached to the annulus, and is somewhat stiffer than the posterior leaflet (that is otherwise attached to the more mobile posterior lateral mitral annulus). The anterior leaflet protects approximately two-thirds of the valve. The anterior leaflet takes up a larger part of the annulus and is generally considered to be "larger" than the posterior leaflet (although the posterior leaflet has a larger surface area). In a healthy mitral valve, then, the anterior and posterior leaflets are asymmetric.

Ideally, the leaflets of a heart valve move apart from each other when the valve is in an open position, and meet or "coapt" when the valve is in a closed position. Problems that may develop with valves include stenosis in which a valve does not open properly, and/or insufficiency or regurgitation in which a valve does not close properly. Stenosis and insufficiency may occur concomitantly in the same valve. The effects of valvular dysfunction vary, with regurgitation or backflow typically having relatively severe physiological consequences to the patient.

Diseased or otherwise deficient heart valves can be repaired or replaced using a variety of different types of heart valve surgeries. One conventional technique involves an open-heart surgical approach that is conducted under general anesthesia, during which the heart is stopped and blood flow is controlled by a heart-lung bypass machine.

More recently, minimally invasive approaches have been developed to facilitate catheter-based implantation of the valve prosthesis on the beating heart, intending to obviate the need for the use of classical sternotomy and cardiopulmonary bypass. In general terms, an expandable prosthetic valve is compressed about or within a catheter, inserted inside a body lumen of the patient, such as the femoral artery, and delivered to a desired location in the heart.

The heart valve prosthesis employed with catheter-based, or transcatheter, procedures generally includes an expandable multi-level frame or stent that supports a valve structure having a plurality of leaflets. The frame can be contracted during percutaneous transluminal delivery, and expanded upon deployment at or within the native valve. One type of valve stent can be initially provided in an expanded or uncrimped condition, then crimped or compressed about a balloon portion of a catheter. The balloon is subsequently inflated to expand and deploy the prosthetic heart valve. With other stented prosthetic heart valve designs, the stent frame is formed to be self-expanding. With these systems, the valved stent is crimped down to a desired size and held in that compressed state within a sheath for transluminal delivery. Retracting the sheath from this valved stent allows the stent to self-expand to a larger diameter, fixating at the native valve site. In more general terms, then, once the prosthetic valve is positioned at the treatment site, for instance within an incompetent native valve, the stent frame structure may be expanded to hold the prosthetic valve firmly in place. One example of a stented prosthetic valve is disclosed in U.S. Pat. No. 5,957,949 to Leonhardt et al., which is incorporated by reference herein in its entirety.

The actual shape and configuration of any particular transcatheter prosthetic heart valve is dependent, at least to some extent, upon the valve being replaced or repaired (i.e., mitral valve, tricuspid valve, aortic valve, or pulmonary valve). The stent frame must oftentimes provide and maintain (e.g., elevated hoop strength and resistance to radially compressive forces) a relatively complex shape in order to achieve desired fixation with the corresponding native anatomy. Moreover, the stent frame must have a robust design capable of traversing the tortuous path leading to the native valve annulus site. These constraints, as well other delivery obstacles such as difficulties in precisely locating and rotationally orienting the prosthetic valve relative to the native annulus, dictate that in some instances, it is beneficial to utilize a valve structure with the prosthesis that purposefully differs from the native (healthy) valve structure or leaflets. For example, the transcatheter prosthetic heart valve may incorporate a symmetric valve structure for replacing an asymmetric native valve, an asymmetric valve structure to replace a symmetric native valve, a valve structure having a greater or lesser number of leaflets than the native valve, a valve structure having leaflet shapes differing from the native valve, etc. These same design choices can arise in the context of other intraluminal prosthetic valves.

While the so-configured prosthetic valve can thus achieve the intended benefits (such as ease of implant) along with long term viable performance as a functioning valve, in some instances other concerns may arise. For example, in many cases, the normally healthy native valve functions to not only open and close, but also effectuates a certain velocity profile in the blood flow exiting the valve. For example, in a healthy mitral valve, the asymmetric, bi-cuspid nature (and the coaptation mechanism of the larger anterior leaflet) results in vortices being formed in the left ventricle during filling. These vortices help synchronize the heart beat and aid in efficient ventricular ejection. A prosthetic mitral valve that does not directly mimic these attributes of the native mitral valve may not generate the normal vortical flow pattern, possibly leading to complications. The failure of a prosthetic valve to account for the natural hemodynamics of the blood through and from other valves of the human body can give rise to similar concerns.

Other concerns relate to possible stasis and thrombus formation at the prosthetic valve resulting from localized regions of turbulent or stagnant flow.

Although there have been multiple advances in transcatheter prosthetic heart valves (and other intraluminal valves) and related delivery systems and techniques, there is a continuing need to provide a valved prosthesis with improved flow profiles.

SUMMARY

Some aspects of the present disclosure relate to a prosthetic valve having an inflow end opposite an outflow end, and comprising a stent frame, a valve structure, and a baffle structure. The stent frame defines a lumen. The valve structure is disposed within the lumen and is configured to define an inflow side and an outflow side. An outflow track is established within the lumen downstream of the outflow side and along which fluid (e.g., blood) flow from the valve structure will progress following implant. The baffle structure is connected to the stent frame proximate and downstream of the valve structure outflow side. With this construction, the baffle structure will modify or manipulate a natural profile of blood flow exiting the valve structure to eliminate or reduce turbulent and/or stagnant regions as the blood flow subsequently interfaces with the stent structure or other regions of the prosthetic valve. By reducing or eliminating turbulence and/or stagnant flow, a likelihood of thrombus formation is reduced. In some embodiments, the baffle structure is configured and located to encourage laminar or near-laminar flow.

Other aspects of the present disclosure are directed toward a method of regulating fluid (e.g., blood flow) flow through a body vessel of a patient. The method includes implanting a prosthetic valve within the body vessel. The prosthetic valve has an inflow end opposite an outflow end, and includes a stent frame, a valve structure, and a baffle structure. The stent frame defines a lumen. The valve structure is disposed within the lumen and is configured to define an inflow side and an outflow side. An outflow track is established within the lumen downstream of the outflow side and along which fluid flow from the valve structure can progress. The baffle structure is connected to the stent frame downstream of the outflow side, and in some embodiments is configured and located to encourage laminar or near-laminar flow. Following the step of implanting the prosthetic valve, fluid flow within the body vessel is naturally directed to the inflow side. The valve structure functions to alternately allow and occlude fluid flow between the inflow and outflow sides. Further, the baffle structure functions to reduce or eliminate occurrences of stagnant or turbulent flow as the fluid flow subsequently interfaces with the stent frame or other regions of the prosthetic valve.

DETAILED DESCRIPTION

Figure 1A:
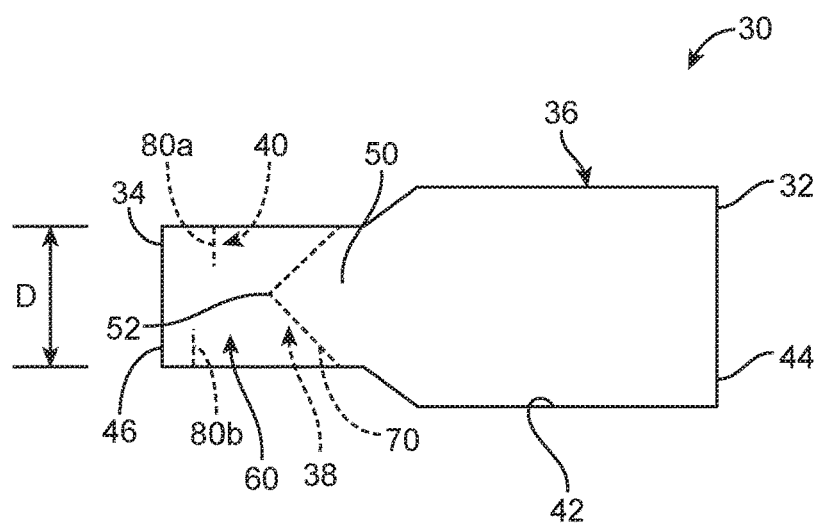
FIG. 1A is a schematic side view of a prosthetic valve in accordance with principles of the present disclosure and in a normal, expanded condition.

Specific embodiments of the present disclosure are now described with reference to the figures, wherein like reference numbers indicate identical or functionally similar elements. The terms "distal" and "proximal" are used in the following description with respect to a position or direction relative to the treating clinician. "Distal" or "distally" are a position distant from or in a direction away from the clinician. "Proximal" and "proximally" are a position near or in a direction toward the clinician. As used herein with reference to an implanted valve prosthesis, the terms "distal", "outlet", and "outflow" are understood to mean downstream to the direction of blood flow, and the terms "proximal", "inlet", or "inflow" are understood to mean upstream to the direction of blood flow. In addition, as used herein, the terms "outward" or "outwardly" refer to a position radially away from a longitudinal axis of a frame of the valve prosthesis and the terms "inward" or "inwardly" refer to a position radially toward a longitudinal axis of the frame of the valve prosthesis. As well the terms "backward" or "backwardly" refer to the relative transition from a downstream position to an upstream position and the terms "forward" or "forwardly" refer to the relative transition from an upstream position to a downstream position.

The following detailed description of prosthetic valves of the present disclosure is merely exemplary in nature and is not intended to limit the disclosure or the application and uses of the prosthetic valves of the present disclosure. Although the description is in the context of treatment of heart valves such as the mitral valve, the prosthetic valves of the present disclosure also may be used in any other body passageways, organs, etc., where it is deemed useful. Furthermore, there is no intention to be bound by any expressed or implied theory presented in the present disclosure.

As referred to herein, stented prosthetic valves, such as stented transcatheter prosthetic heart valves, of the present disclosure may assume a wide variety of different configurations, such as a bioprosthetic heart valve having tissue leaflets or a synthetic heart valve having polymeric, metallic or tissue-engineered leaflets, and can be specifically configured for replacing any of the four valves of the human heart.

Thus, the stented prosthetic heart valves of the present disclosure can be generally used for replacement of a native mitral, aortic, pulmonic or tricuspid valve, or to replace a failed bioprosthesis, such as in the area of a mitral valve or an aortic valve, for example.

In general terms, the stented prosthetic valves (or more simply, "prosthetic valves") of the present disclosure include a stent or stent frame having an internal lumen maintaining a valve structure (tissue or synthetic), with the stent frame having a normal, expanded condition or arrangement and collapsible to a compressed condition or arrangement for loading within a delivery device. The stent frame is normally constructed to self-deploy or self-expand when released from the delivery device. For example, the stents or stent frames are support structures that comprise a number of struts or wire segments arranged relative to each other to provide a desired compressibility and strength to the prosthetic heart valve. The struts or wire segments are arranged such that they are capable of self-transitioning from a compressed or collapsed condition to a normal, radially expanded condition. The struts or wire segments can be formed from a shape memory material, such as a nickel titanium alloy (e.g., Nitinol™). The stent frame can be laser-cut from a single piece of material, or can be assembled from a number of discrete components.

Figure 1B:
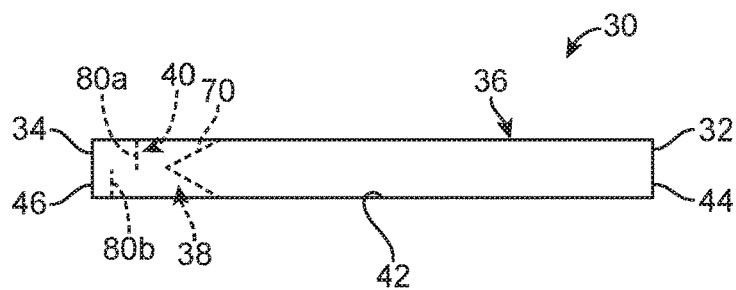
FIG. 1B is a schematic side view of the prosthetic valve of FIG. 1A and in a compressed condition.
Figure 1C:
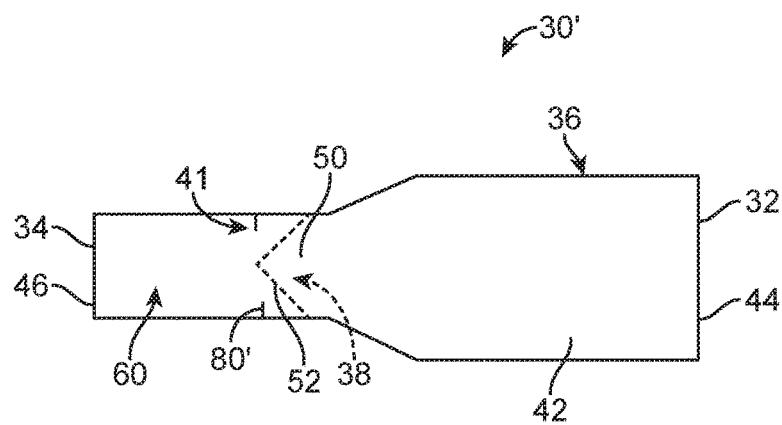
FIG. 1C is a schematic side view of another prosthetic valve in accordance with principles of the present disclosure.

With the above understanding in mind, one non-limiting example of a stented prosthetic valve 30 in accordance with principles of the present disclosure is schematically illustrated in FIG. 1A. As a point of reference, the prosthetic valve 30 is represented in a normal or expanded condition in the view of FIG. 1A; FIG. 1B represents the prosthetic valve 30 in a compressed condition (e.g., when compressively retained within an outer catheter or sheath). The prosthetic valve 30 has or defines an inflow end 32 opposite an outflow end 34, and includes a stent or stent frame 36, a valve structure 38, and one or more baffle structures, such as a vortical flow baffle structure 40 (referenced generally). Alternatively or in addition, and as schematically shown for the alternative prosthetic valve 30' of FIG. 1C, the baffle structure of the present disclosure can be a laminar flow baffle structure 41. Details on the various components are provided below. In general terms, the stent frame 36 defines a lumen 42, an inflow margin 44 and an outflow margin 46 opposite the inflow margin 44. In the exemplary embodiments of FIGS. 1A-1C, the inflow margin 44 of the stent frame 36 serves as or defines the inflow end 32 of the prosthetic valve 30, and the outflow margin 46 serves as or defines the outflow end 34. In other embodiments, one or more bodies of the prosthetic valve 30 project beyond (in the downstream direction) the outflow margin 46 of the stent frame 36 to define or serve as the outflow end 34 of the prosthetic valve 30, and/or upstream of the inflow margin 44 to define the inflow end 32.

The valve structure 38 is disposed within the lumen 42, and is configured to define an inflow side 50 and an outflow side 52 opposite the inflow side 50. An outflow track 60 is established within the lumen 42 downstream of the outflow side 52 and along which fluid flow (e.g., blood flow) from the valve structure 38 progresses during use (in being understood that in the view of FIG. 1A, the valve structure 38 is in a closed state or position). The vortical flow baffle structure 40 is connected to the stent frame 36 and in some embodiments projects into the outflow track 60. As described in greater detail below, the vortical flow baffle structure 40 is configured and located to manipulate fluid flow from the valve structure 38, for example affecting a velocity profile of the fluid flow to be or include vortical flow. In other embodiments described below, the laminar flow baffle structure 41 is provided, configured and located to manipulate fluid flow immediately at the outflow side 52, for example modifying the blood flow in and around the prosthetic valve 30 to reduce or eliminate turbulent (or stagnant) regions that might otherwise lead to thrombus. In yet other embodiments, the prosthetic valves of the present disclosure include both the vortical flow baffle structure 40 (for inducing vortical flow) and the laminar flow baffle structure 41 (for reducing or eliminating turbulent flow at target areas).

The stent frame 36 can assume any of the forms mentioned above, and is generally constructed so as to be expandable from the compressed condition (FIG. 1B) to the normal, expanded condition (FIG. 1A). The stent frame 36 can have a lattice or cell-like structure. The stent frame 36 can be made from stainless steel, a pseudo-elastic metal such as a nickel titanium alloy or Nitinol™, or a so-called super alloy, which may have a base metal of nickel, cobalt, chromium, or other metal. In some embodiments, the stent frame 36 is self-expanding to return to the normal expanded condition from the compressed condition. "Self-expanding" as used herein means that the stent frame 36 has a mechanical memory to return to the normal or expanded condition. Mechanical memory can be imparted to the wire or tubular structure that forms the stent frame 36 by thermal treatment to achieve a spring temper in stainless steel, for example, or to set a shape memory in a susceptible metal allow, such as Nitinol, or a polymer, such as any of the polymers disclosed in US Application Publication No. 2004/0111111 to Lin, which is incorporated by reference herein in its entirety. In other embodiments, the stent frame 36 need not be of a self-expanding construction. Regardless, the stent frame 36 can be formatted to assume a variety of different shapes in the normal, expanded condition corresponding to the native anatomy at which the prosthetic valve 30 will be implanted and that may or may not be implicated by the general shapes reflected in FIG. 1A (e.g., the prosthetic valves of the present disclosure need not have the stepped-down shape shown or can have a more complex shape).

The valve structure 38 can assume a variety of forms, and can be formed, for example, from one or more biocompatible synthetic materials, synthetic polymers, autograft tissue, homograft tissue, xenograft tissue, or one or more other suitable materials. In some embodiments, the valve structure 38 can be formed, for example, from bovine, porcine, equine, ovine and/or other suitable animal tissues. In some embodiments, the valve structure 38 can be formed, for example, from heart valve tissue, pericardium, and/or other suitable tissue. Non-limiting examples of prosthetic valves and/or prosthetic valve features that may be used in accordance with one or more embodiments of the present disclosure are described in U.S. patent application Ser. No. 14/175,100, filed Feb. 7, 2014, entitled "HEART VALVE PROSTHESIS", and which patent application is hereby incorporated by reference in its entirety to the extent that it does not conflict with the disclosure presented herein.

In some embodiments, the valve structure 38 can include or form one or more leaflets 70. For example, the valve structure 38 can be in the form of a tri-leaflet bovine pericardium valve, a bi-leaflet valve, or another suitable valve. In some constructions, the valve structure 38 can comprise two or three leaflets that are fastened together at enlarged lateral end regions to form commissural joints, with the unattached edges forming coaptation edges of the valve structure 38. The leaflets 70 can be fastened to a skirt that in turn is attached to the stent frame 36. The upper ends of the commissure points can define the inflow side 50. Regardless, the valve structure 38 transitions between a closed state (reflected in FIG. 1A), in which the valve structure 38 closes the lumen 44 and prevents fluid flow there through (e.g., from the outflow end 34 to the inflow end 32), and an open state shown in FIG. 2 (described in greater detail below), in which the valve structure 38 permits fluid flow through the lumen 44 (e.g., from the inflow end 32 to the outflow end 34).

The baffle structures of the present disclosure can assume a wide variety of forms, and includes at least one baffle member 80. In some embodiments, the baffle structure can include a plurality of baffle members, with FIG. 1A reflecting provision of first and second baffle members 80a, 80b for the vortical flow baffle structure 40 (it being understood that three or more baffle members can be provided in yet other embodiments). Regardless of the number included, with optional embodiments in which the vortical flow baffle structure 40 is provided (as in FIGS. 1A and 1B), the baffle member(s) 80 of the vortical flow baffle structure 40 collectively serve to affect or influence fluid flow from the valve structure 38 as it progress from the outflow side 52, including creating or generating a velocity profile in the fluid flow exiting the outflow end 34 that is non-uniform, including a flow profile that includes vortices (or "vortical flow"). In related embodiments, the vortical flow baffle structure 40 is configured to affect or create a vortex ring or toroidal vortex in the fluid flow.

Figure 2:
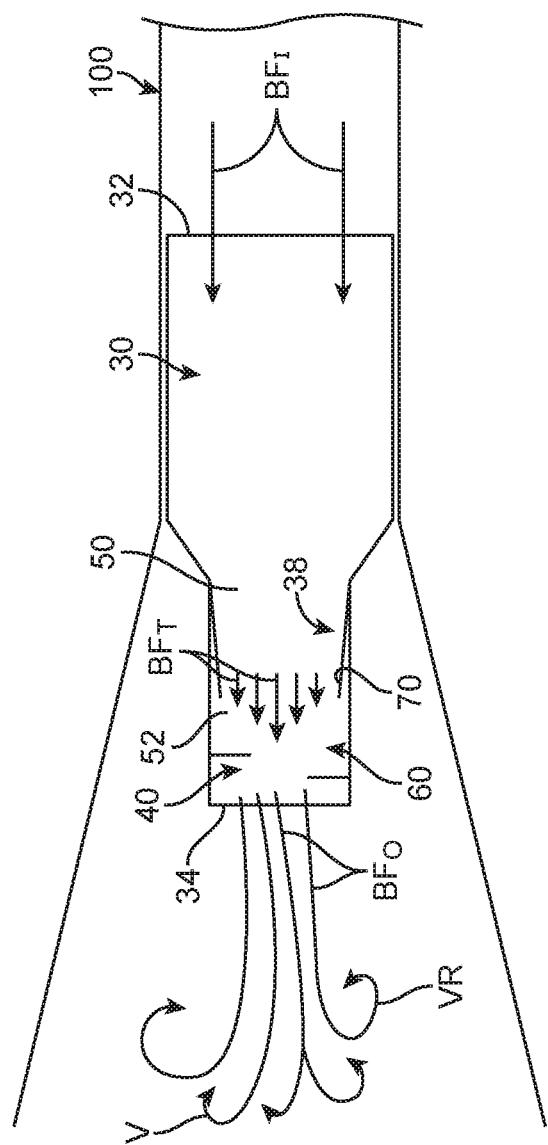
FIG. 2 is a schematic cross-sectional view of the prosthetic valve of FIG. 1A located within a body vessel.
Figure 3:
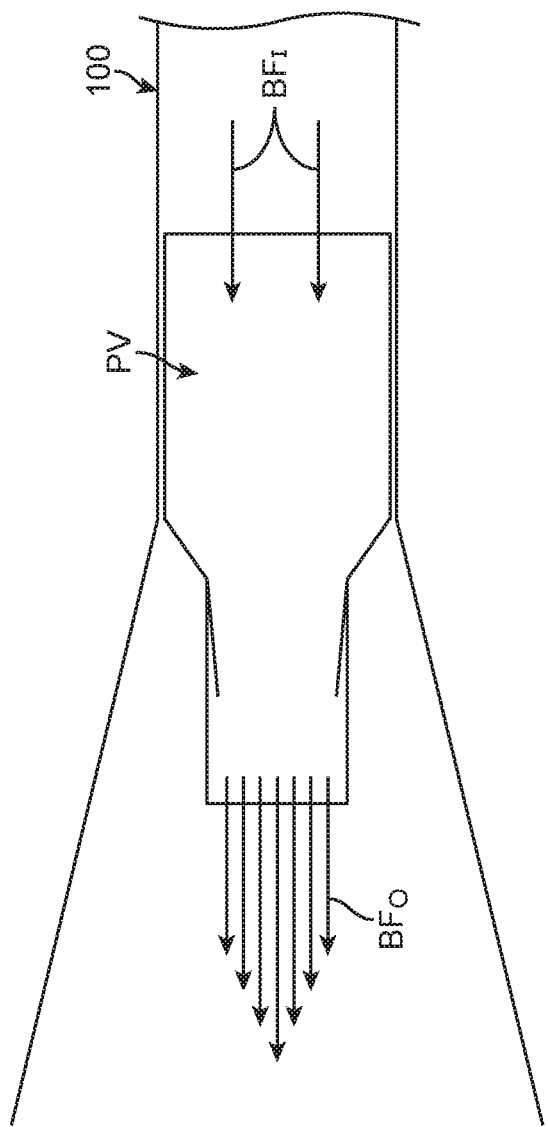
FIG. 3 is a schematic cross-sectional view of a prior art prosthetic valve located within the body vessel of FIG. 2.

By way of further explanation with respect to the non-limiting embodiments in which the vortical flow baffle structure 40 is provided, FIG. 2 represents the prosthetic valve 30 implanted or located within a generic bodily vessel 100. Fluid flow (e.g., blood flow, other liquid flow, air or other gas flow, etc.) within the vessel 100 is naturally directed toward the inflow end 32, as identified by arrows $BF_I$. In the view of FIG. 2, the valve structure 38 is an open state or condition. The open state or condition can be achieved in various manners depending upon a particular construction of the prosthetic valve 30. In some embodiments, the valve structure 38 has a passive configuration, and naturally transitions to the open state when a pressure at the inflow side 50 is greater than a pressure at the outflow side 52 (identified in FIG. 1A). Regardless, in the open state, the valve structure 38 permits the fluid flow $BF_I$ to pass through or between the leaflets 70, progressing from the outflow side 52 into the outflow track 60. Fluid flow within the outflow track 60 upstream of the vortical flow baffle structure 40 is generally identified by arrows $BF_T$. Prior to interfacing with the vortical flow baffle structure 40, the fluid flow $BF_T$ naturally has a relatively uniform velocity profile corresponding with the native or natural fluid flow velocity profile within the vessel 100 were the prosthetic valve 30 not present (e.g., may or may not be laminar flow, but does not include vortices or vortical flow). As the fluid flow progresses through the outflow track 60 and interfaces with the vortical flow baffle structure 40, the vortical flow baffle structure 40 manipulates the fluid flow, such that the fluid flow exiting the outflow end 34 (identified the arrows $BF_O$) includes vortices V. In some embodiments, the vortical flow baffle structure 40 is configured to create a complex vortex arrangement in the fluid flow $BF_O$ exiting the outflow end 34, as schematically illustrated by the arrows in FIG. 2. The so-induced flow or velocity profile is or includes a vortex ring or toroidal vortex VR in an exemplary embodiment. In comparison, FIG. 3 illustrates a velocity profile of fluid flow exiting a prosthetic valve PV that is otherwise identical to the prosthetic valve 30 of FIG. 2 except that the vortical flow baffle structure 40 is omitted. The incoming fluid flow $BF_I$ and the fluid flow $BF_T$ immediately downstream of the outflow side 52 (of the valve structure 38) are identical in both views. However, because the prosthetic valve PV of FIG. 3 does not include a baffle structure configured to overtly manipulate the fluid flow, the fluid flow exiting the prosthetic valve PV has a relatively uniform flow velocity profile, and does not include any substantive vortices or vortex ring.

Returning to FIG. 2, and again with respect to non-limiting embodiments in which the optional vortical flow baffle structure 40 is provided, it is recognized that a number of parameters can affect the profile of fluid flow exiting the prosthetic valve 30 apart from the vortical flow baffle structure 40. For example, the size (e.g., length and inner diameter) of the stent frame 36, frictional attributes of the valve structure 38, flow characteristics of the incoming fluid flow $BF_I$ at the particular native vessel, etc. The vortical flow baffle structures 40 of some embodiments of the present disclosure are configured with these other parameters in mind, functioning to cause a marked change in the velocity profile in the fluid flow exiting the prosthetic valve 30, for example inducing vortical flow under circumstance where, but for the vortical flow baffle structure 40, substantive vortices V or the vortex ring VR would not occur.

The baffle structures 40, 41, and in particular the baffle member(s) 80, of the present disclosure can assume a wide variety of forms. The baffle member(s) 80 can be any device (e.g., a plate, wall, screen, partition, paddle, etc.) arranged within the outflow track 60 or downstream of the outflow margin 46 of the stent frame 36 so as to deflect, check or regulate flow or passage of fluid (e.g., blood), but that does not entirely occlude fluid flow. For example, the baffle member(s) 80 can be a solid or perforated plate formed of a rigid, compliant or semi-complaint biocompatible material. The baffle member(s) 80 can have a symmetric or asymmetric shape and can have a profile tailored to generate the desired velocity profile, for example in accordance with the expected conditions at the native vessel at which the prosthetic valve 30 is to be implanted. Further, a location of the baffle member(s) 80 of the vortical flow baffle structure 40 relative to the valve structure outflow side 52 (e.g., axial distance or spacing between the outflow side 52 and the baffle member(s) 80) can also be tailored to optimize the exiting fluid flow profile relative to the native anatomy at which the prosthetic valve 30 will be implanted. Where two (or more) of the baffle members 80 are provided, the baffle members 80 can have identical or differing shapes, can be asymmetric in shape and/or can be mounted to the stent frame 36 off-plane from one another. The baffle member(s) 80 can be connected (directly or indirectly) to the stent frame 36 in various fashions, such as by an appropriate connection device (e.g., elasticated sutures), welding, adhesive, etc.

In addition to material selection, profile shape and porosity, an ability of the baffle member(s) 80 of the vortical flow baffle structure 40 to, in some non-limiting embodiments, induce vortical flow at desired levels and with a desired shape (e.g., vortex ring or toroidal vortex) without overtly obstructing fluid flow is, in some embodiments, a function of an extent to which the baffle member(s) 80 project across a diameter of the outflow track 60 (and thus project into the fluid flow profile). More particularly, and with reference to the non-limiting example of FIG. 1A, the outflow track 60 has a diameter D in the normal, expanded condition of the stent frame 36 (i.e., a diameter of the lumen 44 downstream of the valve structure 38). Extension of each of the one or more baffle members 80 of the vortical flow baffle structure 40 includes a radial component relative to an axial center line of the stent frame 36. For example, in some embodiments, at least one of the baffle members 80 extends in the radial direction across at least 10% of the outflow track diameter D, in other embodiments, at least 20%, and in yet other embodiments at least 30%. In related embodiments, the outflow track 60 can be described as defining an area in a plane perpendicular to a longitudinal axis of the stent frame 36. Relative to a plane perpendicular to the longitudinal axis and passing through one of the baffle members 80, the baffle member 80 occupies at least 10% of the outflow track area, in other embodiments at least 20%, and in yet other embodiments at least 30%; in related embodiments, the baffle member 80 occupies not more than 95% of the outflow track area, in other embodiments not more than 90%, and in yet other embodiments not more than 85%. Within these design parameters, the baffle member 80 is configured, in some non-limiting embodiments, to sufficiently interact with fluid flow to induce vortical flow, but will not overtly obstruct fluid flow to levels below the needs of the patient.

Figure 4:
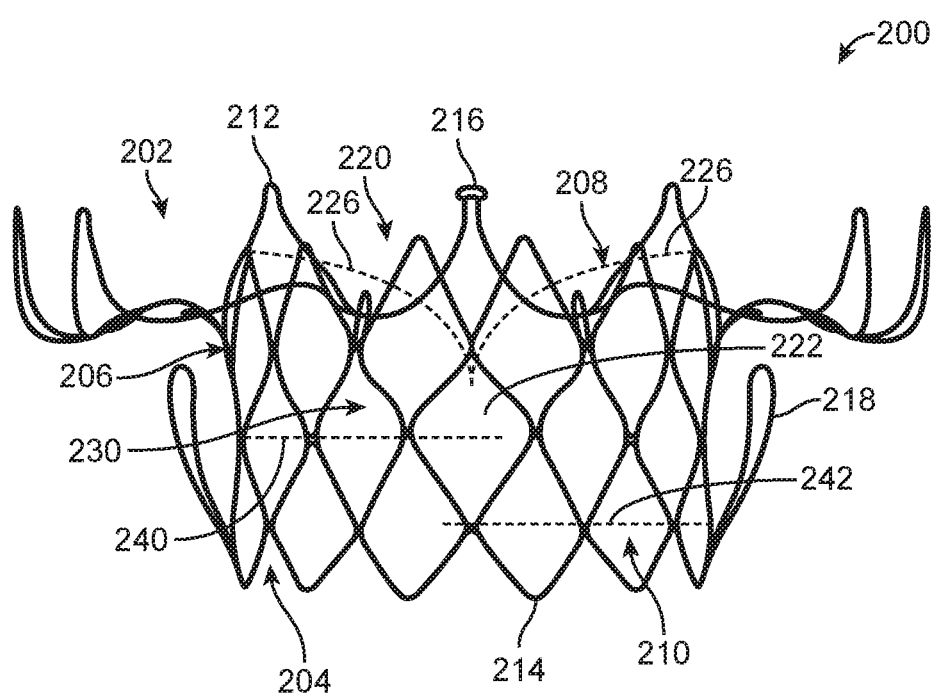
FIG. 4 is a side view of a prosthetic mitral valve in accordance with principles of the present disclosure and useful as a prosthetic mitral valve.

As indicated above, the prosthetic valves of the present disclosure can include a baffle structure configured or tailored to the particular native valve being addressed, for example to effectuate a flow profile akin to or mimicking the native or natural flow profile otherwise normally occurring at the native (healthy) valve anatomy in some non-limiting embodiments. For example, in some embodiments the prosthetic valve of the present disclosure is intended to repair or replace a native mitral valve. FIG. 4 illustrates one embodiment of a prosthetic mitral valve 200 in accordance with principles of the present disclosure that defines an inflow end 202 opposite an outflow end 204, and includes a stent frame 206, a valve structure 208 and a vortical flow baffle structure 210 (referenced generally).

The stent frame 206 can have any of the constructions described above, and generally defines a lumen, an inflow margin 212 and an outflow margin 214 opposite the inflow end 212. In the exemplary embodiment of FIG. 4, the stent frame inflow and outflow margins 212, 214 serve as or define the inflow ends 202, 204, respectively, of the prosthetic valve 200. The stent frame 206 optionally includes or forms additional features useful for connection to a delivery device, such as crowns or eyelets 216. Further, the stent frame 206 can optionally include or carry additional support structures, such as one or more support arms 218. The stent frame 206 may also be configured to provide axial fixation by creating tensioning of chordae tendinae of the native mitral valve space.

The valve structure 208 (shown schematically in phantom) is disposed within the lumen and is configured to define an inflow side 220 and an outflow side 222 opposite the inflow side 220. The valve structure 208 can have any of the constructions described above and in some embodiments optionally is a uniform tricuspid valve structure, including three leaflets 226 (two of which are represented in FIG. 4). Alternatively, the valve structure 208 can provide more or less than three of the leaflets 226. Regardless, an outflow track 230 (referenced generally) is established within the lumen downstream of the outflow side 222 and along which fluid flow (e.g., blood flow) from the valve structure 208 progresses following implant.

The vortical flow baffle structure 210 is connected to the stent frame 206 and optionally projects into the outflow track 230 in some embodiments. With the exemplary embodiment of FIG. 4, the vortical flow baffle structure 210 includes first and second baffle members 240, 242. The baffle members 240, 242 can each assume any of the forms described above and are longitudinally or axially spaced from one another. The baffle members 240, 242 can project from diametrically opposite sides of the stent frame 206, each optionally extending across at least 10%, and less than 90%, of a diameter of the outflow track 230 as described above. Further, a gap 244 is established between the baffle members 240, 242 through which fluid flow can readily occur from the outflow side 222 of the valve structure 204 to (and outwardly from) the outflow end 204.

Figure 5:
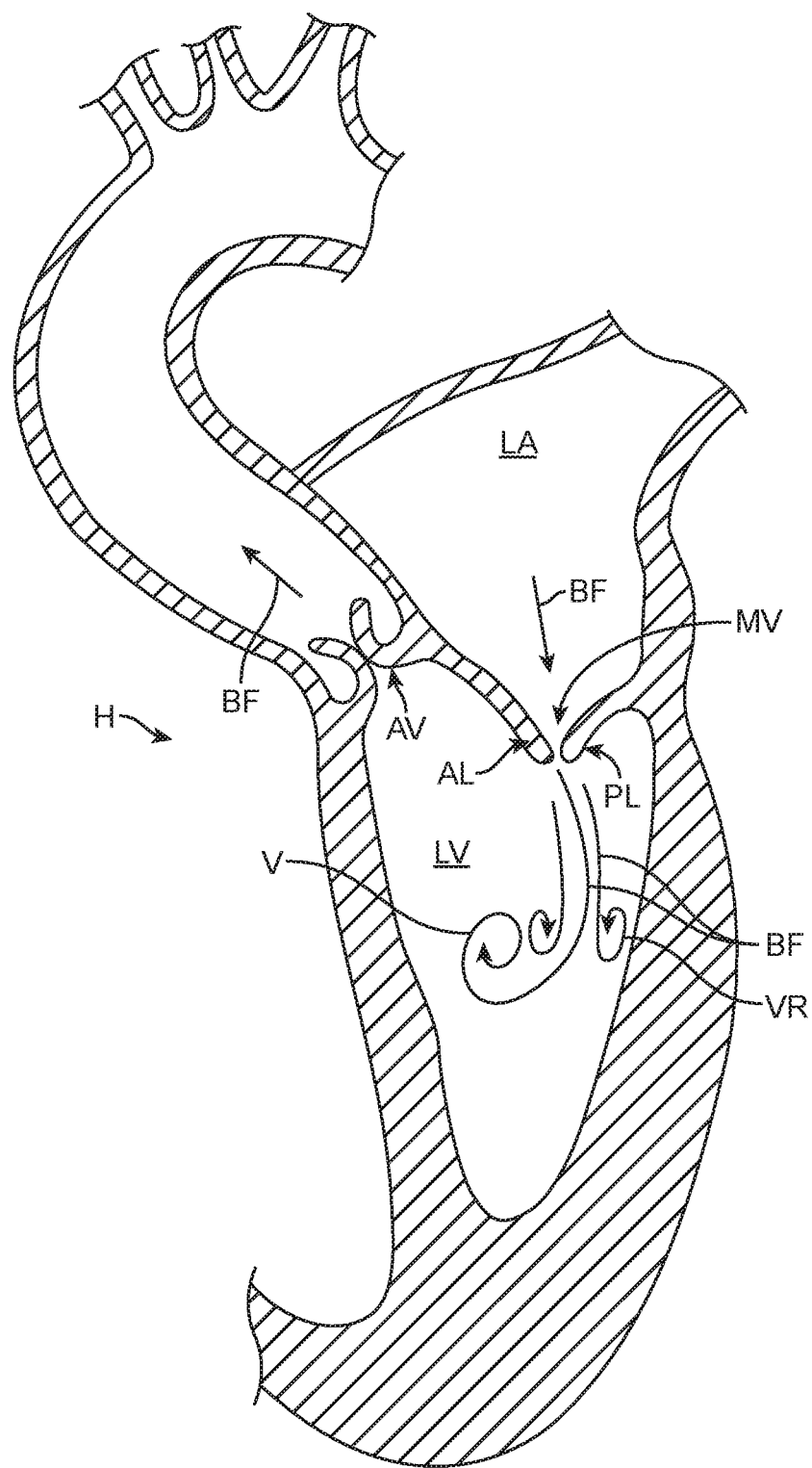
FIG. 5 is a simplified cross-sectional view of a portion of a human heart.

The stent frame 206 is sized and shaped (in the natural, expanded state of FIG. 4) in accordance with the native anatomy for replacing or repairing a mitral valve. As a point of reference, FIG. 5 illustrates a portion of a heart H including a left atrium LA, a left ventricle LV, a mitral space MV and an aortic valve AV. The mitral space MV includes an anterior leaflet AL and a posterior leaflet PL. Blood flow BF is depicted with directional arrows in FIG. 5 in the left atrium LA, into the left ventricle LV through the mitral valve space MV, and into the aorta through the aortic valve AV. When the native mitral valve is operating properly, the native leaflets AL, PL will generally function in such a way that blood flows toward the left ventricle LV when the leaflets AL, PL are in an open position, and so that blood is prevented from moving toward the left atrium LA when the leaflets AL, PL are in a closed position. As shown, the anterior leaflet AL (along with other anatomical features such as the mitral valve's coaptation mechanism) of a healthy native mitral valve naturally induces vortical flow into the blood flow BF as it enters the left ventricle LV in a direction of an apex A of the left ventricle LV, the flow profile including vortices V. The blood flow BF at the left ventricle LV often has a complex vortex arrangement, including a vortex ring or toroidal vortex VR (referenced generally).

Figure 6:
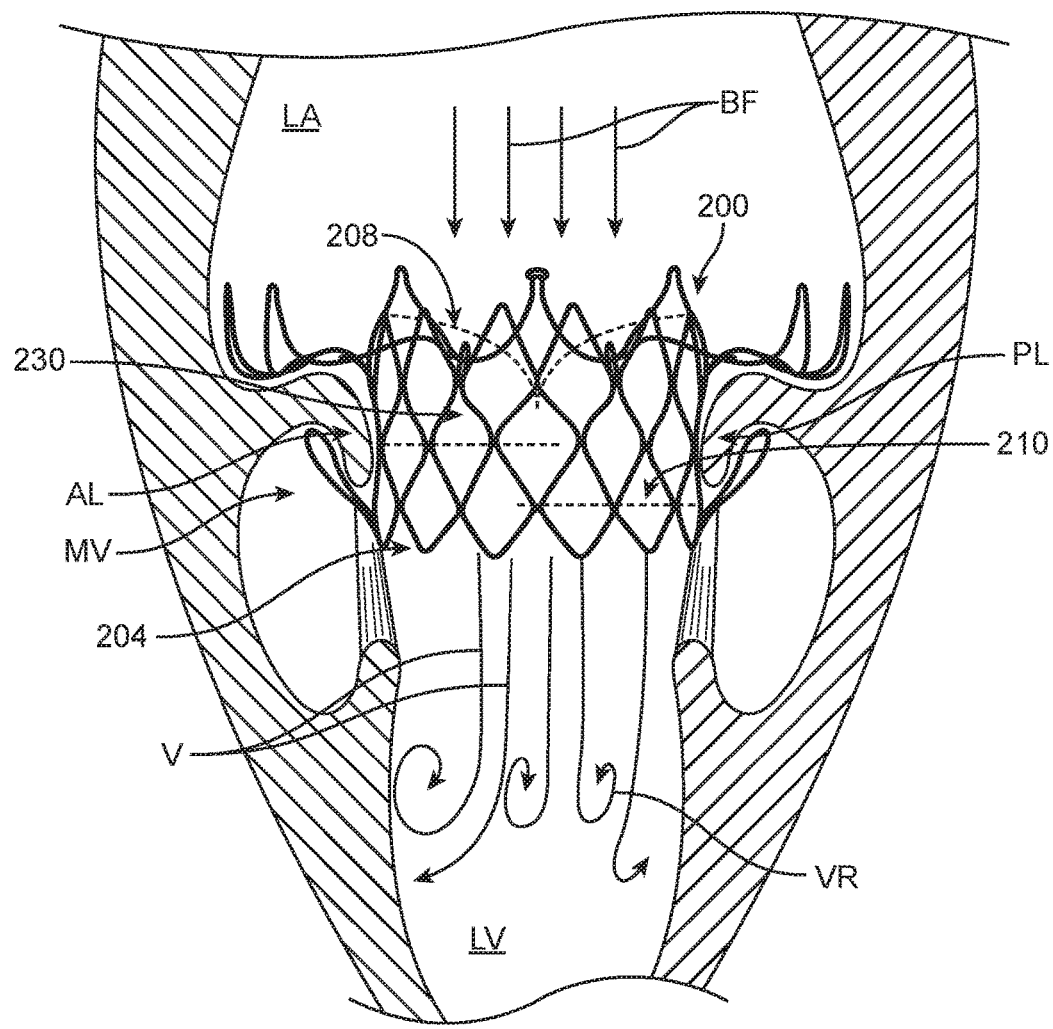
FIG. 6 illustrates the prosthetic valve of FIG. 4 implanted at a mitral valve target location of the heart of FIG. 5.

FIG. 6 illustrates the prosthetic valve 200 following placement or implant within the mitral space MV. The prosthetic valve 200 can be delivered via a transcatheter or percutaneous approach, including the prosthetic valve 200 being compressed within a delivery device, tracked through the patient's vasculature to the mitral space MV, and then caused to expand (e.g., self-expansion or forced expansion such as with a balloon as is known in the art) within the mitral space MV. Transcatheter delivery devices useful with the prosthetic valves of the present disclosure can have a known or conventional form generally providing a retractable outer sheath for releasably containing the compressed prosthetic valve, an inner shaft or tube for supporting the compressed prosthetic valve, and optionally having additional components such as any of the components described, for example, in Yeung et al., U.S. Publication No. 2011/009880; Duffy et al., U.S. Publication No. 2012/0041547; Murray et al., U.S. Publication No. 2012/0310332, the entire teachings of each of which are incorporated herein by reference.

Following placement at the mitral space MV (in which the prosthetic valve 200 may push the native leaflets AL, PL out of the mitral space MV, or the native leaflets can be surgically removed), the prosthetic valve 200 functions to permit blood flow from the left atrium LA to the left ventricle LV when the valve structure 208 is in the open state, and to prevent blood flow from the left ventricle LV to the left atrium LA when the valve structure 208 is in the closed state. Blood flow in the valve open state is illustrated by arrows BF as progressing from the left atrium LA, through the prosthetic valve 200, and into the left ventricle LV. In this regard, as the blood flow progresses along the outflow track 230, the vortical flow baffle structure 210 (referenced generally) manipulates the otherwise relatively uniform flow profile and induces vortices into the flow. More particularly, blood flow exiting the outflow end 204 has a vortical flow or velocity profile, including multiple vortices (represented by the arrows V in FIG. 6). In some embodiments, the blood flow exiting the outflow end has a complex vortex arrangement, including a vortex ring or toroidal vortex VR (referenced generally). The vortical flow into the left ventricle LV can have a circular-type flow component as it reaches and interfaces with the apex A (FIG. 5) of the left ventricle LV. It is believed these vortices V help synchronize the heart beat and aid in efficient ventricular ejection. In some embodiments, the vortical flow baffle structure 210 is configured (e.g., construction, location, etc.) to manipulate at least 10% of the blood flow progressing through the outflow track 230, such that at least 10% of the blood flow exiting the outflow end 204 exhibits vertical flow.

Figure 7:
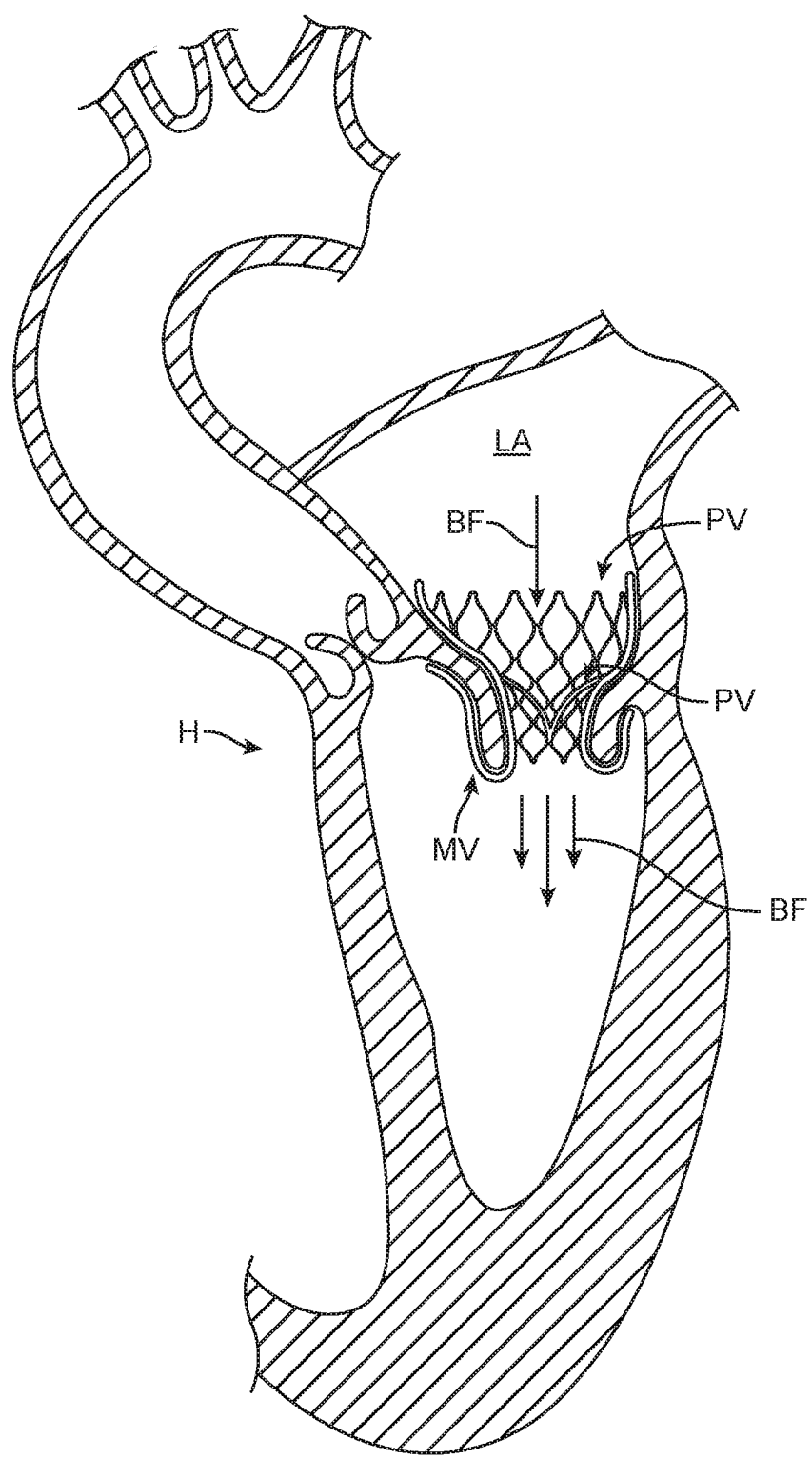
FIG. 7 illustrates a blood flow profile generated by a prior art prosthetic mitral valve implanted at a mitral valve target location of the heart of FIG. 5.

The vortical flow effectuated by the prosthetic valve 200 attempts to mimic the natural velocity flow profile generated by a natural, healthy mitral valve as evidenced by a comparison of FIGS. 5 and 6. However, the prosthetic valve 200 optionally incorporates a tricuspid leaflet valve structure (with the three leaflets optionally being relatively uniform) construction that differs significantly from the asymmetric, bicuspid form of the native mitral valve. Thus, the prosthetic valve 200 can more easily be delivered and located via a transcatheter approach (as compared to a prosthetic mitral valve incorporating an asymmetrical, two leaflet valve structure), while at the same time effectuating a desired vortical blood flow profile. By way of further comparison, FIG. 7 illustrates the heart H with a conventional prosthetic mitral valve PV (i.e., does not include the baffle structure of the present disclosure) implanted to the mitral space MV. The blood flow exiting the prosthetic valve PV has a relatively uniform velocity profile, with insignificant, if any, vortices.

Figure 8:
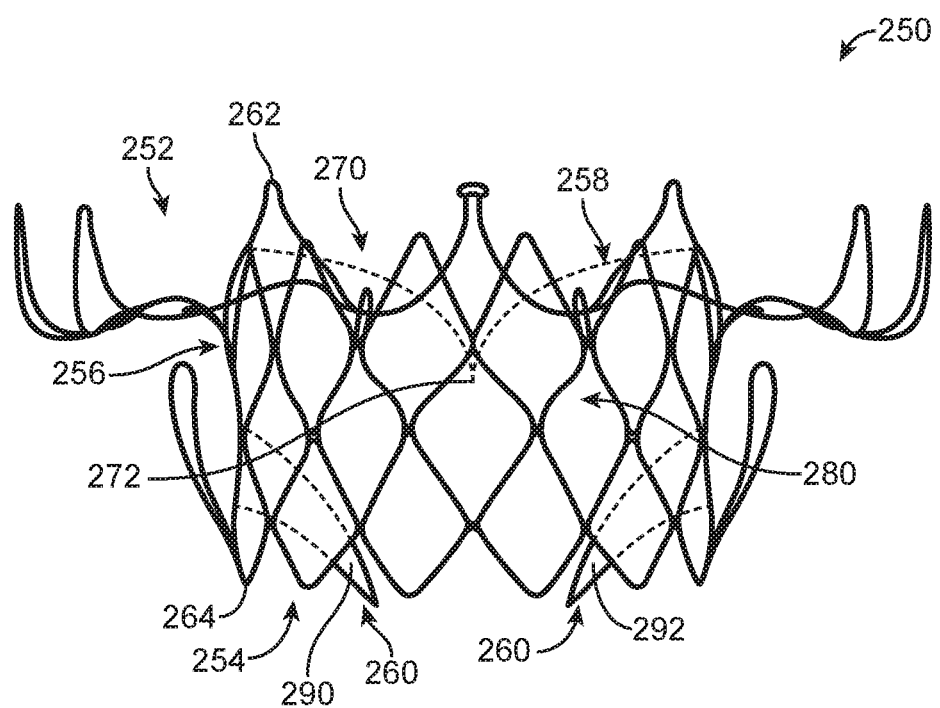
FIG. 8 is a side view of another prosthetic valve in accordance with principles of the present disclosure.

The vortical flow baffle structure 210 described above is but one example of a baffle structure in accordance with principles of some embodiments of the present disclosure configured to induce or create vortical flow, for example including a vortex ring or toroidal vortex. For example, FIG. 8 illustrates another prosthetic valve 250 in accordance with principles of the present disclosure, and defines an inflow end 252 opposite an outflow end 254. The prosthetic valve 250 includes a stent frame 256, a valve structure 258 and a vortical flow baffle structure 260 (referenced generally).

The stent frame 256 and the valve structure 258 can have any of the configurations described elsewhere in this disclosure, and are in no way limited to the constructions possibly implicated by the view of FIG. 8. For example, a shape of the stent frame 256 in the normal, expanded condition can be appropriate for deployment at a native mitral valve anatomy, or alternatively, would be shaped in accordance with any other internal anatomy of the human body. Regardless, the stent frame 256 generally defines a lumen, an inflow margin 262 and an outflow margin 264 opposite the inflow margin 262. In the exemplary embodiment of FIG. 8, the stent frame inflow and outflow margins 262, 264 serve as or define the inflow and outflow ends 252, 254, respectively, of the prosthetic valve 250. Alternatively, a portion of the vortical flow baffle structure 260 can project beyond the outflow margin 264 to define the outflow end 254. The valve structure 258 (drawn schematically in phantom) is disposed within the stent frame lumen, and is configured to provide an inflow side 270 and an outflow side 272 opposite the inflow side 270. An outflow track 280 (referenced generally) is established within the lumen downstream of the outflow side 272 and along which fluid flow from the valve structure 254 progresses following implant.

The vortical flow baffle structure 260 is connected to the stent frame 256 and optionally projects into the outflow track 280. With the exemplary embodiment of FIG. 8, the vortical flow baffle structure 260 includes first and second baffle members 290, 292. In other embodiments, a single one, or more than two, of the baffle members 290, 292 are provided. The baffle members 290, 292 can have any of the forms described above (e.g., solid plate, perforated plate, rigid material, flexible material, etc.). The baffle members 290, 292 can be longitudinally aligned (relative to a longitudinal axis of the stent frame 256) and can be shaped to extend from the stent frame 256 in a generally downstream direction. The baffle members 290, 292 can be identical or can differ in terms of at least shape or size, and can each optionally extend across at least 10%, and less than 90%, of a diameter of the outflow track 280.

Following implant, the prosthetic valve 250 functions in accordance with the above descriptions, with the valve structure 258 transitioning between open and closed states. As fluid flow progresses from the outflow side 272, the fluid flow interfaces with the vortical flow baffle structure 260. The vortical flow baffle structure 260 induces vortices into the fluid flow as the fluid flow exits the outflow end 254 commensurate with the above descriptions, optionally creating a vortex ring or toroidal vortex in the exiting fluid flow.

Figure 9:
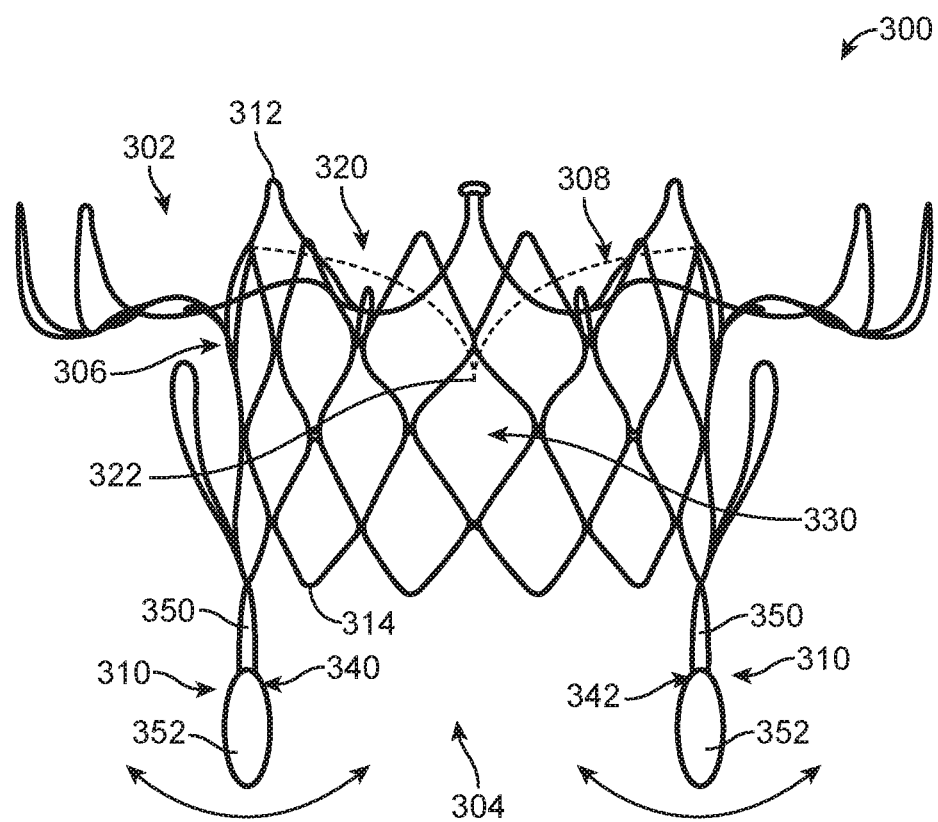
FIG. 9 is a side view of another prosthetic valve in accordance with principles of the present disclosure.

Another embodiment prosthetic valve 300 in accordance with principles of the present disclosure is shown in FIG. 9. The prosthetic valve 300 defines an inflow end 302 opposite an outflow end 304, and includes a stent frame 306, a valve structure 308 and a vortical flow baffle structure 310 (referenced generally).

The stent frame 306 and the valve structure 308 can have any of the configurations described elsewhere in this disclosure, and are in no way limited to the constructions possibly implicated by the view of FIG. 9. For example, a shape of the stent frame 306 in the normal, expanded condition can be appropriate for deployment at a native mitral valve anatomy, or alternatively could be shaped in accordance with any other internal anatomy of the human body. Regardless, the stent frame 302 generally defines a lumen, an inflow margin 312 and an outflow margin 314 opposite the inflow margin 312. The valve structure 308 (drawn schematically in phantom) is disposed within the stent frame lumen, and is configured to provide an inflow side 320 opposite an outflow side 322. An outflow track 330 (referenced generally) is established within the lumen downstream of the outflow side 322 and along with fluid flow from the valve structure 308 progresses following implant.

The vortical flow baffle structure 310 is connected to the stent frame 302. With the exemplary embodiment of FIG. 9, the baffle structure 306 includes first and second baffle members 340, 342. In other embodiments, a single one, or more than two, of the baffle members 340, 342 are provided. The baffle members 340, 342 can have any of the forms described above (e.g., solid plate, perforated plate, rigid material, flexible material, etc.). In some embodiments, the baffle members 340, 342 can have a similar, or even identical, shape, for example the paddle-like shape illustrated in FIG. 9. The baffle members 340, 342 can each include or define a post 350 and a head 352. The optional paddle-like shape is generated by a width of at least a portion of the head 352 being greater than a width of the post 350. The post 350 is pivotably coupled to the stent frame 306, with the head 352 being movable relative to the stent frame 306 with pivoting of the post 350 (represented by arrows in FIG. 9).

Coupling between the post 350 and the stent frame 306 and/or a construction of the baffle members 340, 342 optionally biases the baffle members 340, 342 to a particular orientation relative to the stent frame 306.

In some embodiments, the post 350 is connected to the stent frame 306 at or in close proximity to the outflow margin 314. With this construction, the corresponding head 352 can be located away from, or downstream of, the outflow margin 314 of the stent frame 306 as shown. While the baffle members 340, 342 can, in some embodiment, sufficiently pivot or rotate to bring the corresponding head 352 into the lumen of the stent frame 306, with some embodiments of the present disclosure, including those of FIG. 9, the vortical flow baffle structure 310 effectively defines the outflow end 304 of the prosthetic valve 300 (i.e., the last structure or body of the prosthetic heart valve 300 that interfaces with fluid flowing in the outflow or downstream direction).

Following implant, the prosthetic valve 300 functions in accordance with the above descriptions, including the valve structure 308 transitioning between open and closed states. As fluid progresses from the outflow side 322 of the valve structure 308, the fluid flow interfaces with the vortical flow baffle structure 310. In this regard, the baffle members 340, 342 can naturally move or pivot into the fluid flow path as it exits the outflow margin 314 of the stent frame 306 or can be biased to this position. Regardless, the vortical flow baffle structure 310 induces vortices into the fluid flow as the fluid flow progresses beyond or downstream of the outflow end 304 commensurate with the above descriptions, optionally creating a vortex ring or toroidal vortex in the exiting fluid flow.

Figure 10:
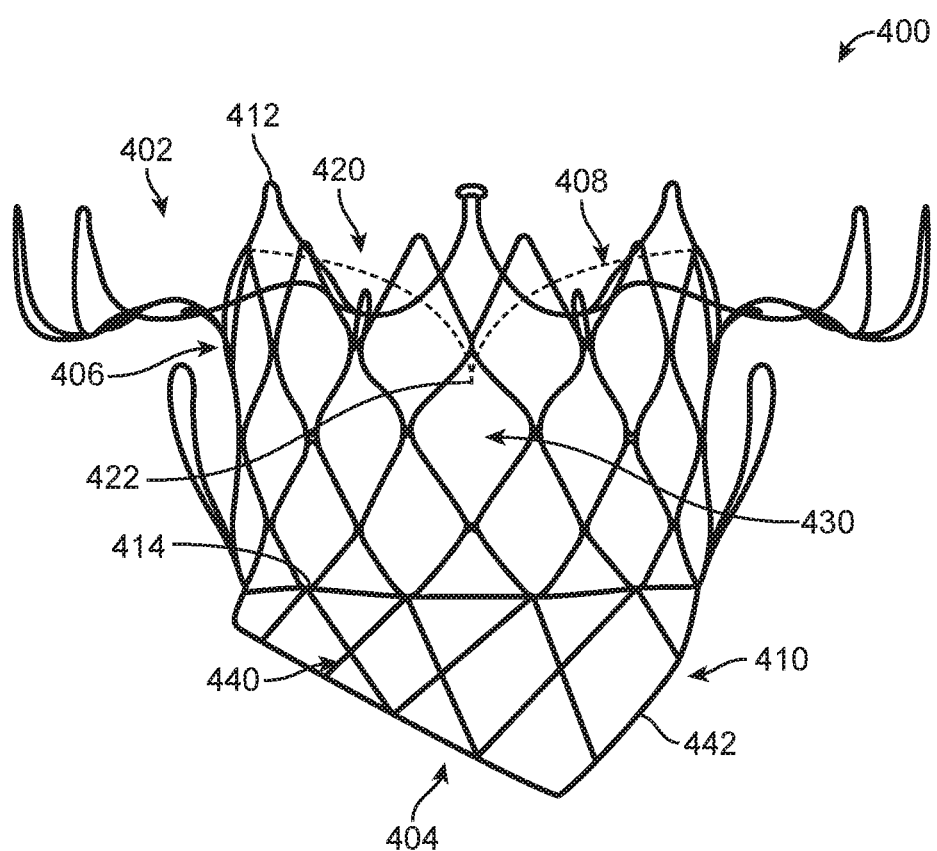
FIG. 10 is a side view of another prosthetic valve in accordance with principles of the present disclosure.

Another embodiment prosthetic valve 400 in accordance with principles of the present disclosure is shown in FIG. 10. The prosthetic valve 400 defines an inflow end 402 opposite an outflow end 404, and includes a stent frame 406, a valve structure 408 and a vortical flow baffle structure 410.

The stent frame 406 and the valve structure 408 can have any of the configurations described elsewhere in this disclosure, and are in no way limited to the constructions possibly implicated by the view of FIG. 10. For example, a shape of the stent frame 406 in the normal, expanded condition can be appropriate for deployment at a native mitral valve anatomy, or alternatively could be shaped in accordance with any other internal anatomy of the human body. Regardless, the stent frame 406 generally defines a lumen, an inflow margin 412 and an outflow margin 414 opposite the inflow margin 412. The valve structure 408 (drawn schematically in phantom) is disposed within the stent frame lumen, and is configured to provide an inflow side 420 opposite an outflow side 422. An outflow track 430 (referenced generally) is established within the lumen downstream of the outflow side 422 and along with fluid flow from the valve structure 408 progresses following implant.

The vortical flow baffle structure 410 is connected to the stent frame 406. With the exemplary embodiment of FIG. 10, the vortical flow baffle structure 410 includes a baffle member 440 in the form of a sleeve or cowl. The baffle member 440 can be formed of a mesh or solid material, and forms at least one side 442 to have a curvature that projects into the fluid flow path exiting the outflow margin 414 of the stent frame 406. Thus, with the embodiment of FIG. 10, the vortical flow baffle structure 410 defines the outflow end 404 of the prosthetic heart valve 400 (i.e., the last or downstream-most structure of the prosthetic heart valve 400 that interfaces with fluid flowing in the outflow or downstream direction).

Following implant, the prosthetic valve 400 functions in accordance with the above descriptions, including the valve structure 408 transitioning between open and closed states. As fluid progresses from the outflow side 422 of the valve structure 408, the fluid flow interfaces with the vortical flow baffle structure 410. More particularly, the baffle member 440 projects into the fluid flow path as it exits the outflow margin 414 of the stent frame 406. The vortical flow baffle structure 410 induces or creates vortices into the fluid flow progressing beyond or downstream of the outflow end 404 commensurate with the above descriptions, optionally creating a vortex ring or toroidal vortex in the fluid flow.

Returning to FIG. 1C, the while some embodiments of the present disclosure include a vortical flow baffle structure, other embodiment prosthetic valves of the present disclosure incorporate a baffle structure in the form of a laminar flow baffle structure, such as the laminar flow baffle structure 41 shown for the prosthetic valve 30'. The laminar flow baffle structure 41 can be located more proximate the outflow side 52 (as compared to the vortical flow baffle structures described above) and is configured to modify or manipulate blood flow locally through the lumen 42 at the outflow track 60 to target areas that might otherwise be subject to stagnant or turbulent flow were the laminar flow baffle structure 41 not present. With these embodiments, the laminar flow baffle structure 41 serves to modify blood flow to reduce or eliminate turbulent regions in and around the prosthetic valve 30' (that might otherwise occur were the inflow baffle structure 41 not present), directing the blood flow into designated areas in order to create laminar or near-laminar flow. Presence of the laminar flow baffle structure 41 may or may not affect a flow profile at the outlet end 34 (as compared to a flow profile were the laminar flow baffle structure 41 not present), and may or may not contribute to formation of vortices at the outlet end 34.

The baffle member(s) 80' provided with the laminar flow baffle structure 41 can assume a variety of forms, including any of the forms described for the vortical flow baffle structures above. For example, in some embodiments, the baffle members 80' of the laminar flow baffle structure 41 can be akin to paddles, the shape and location of which can be optimized (e.g., in terms of effectuating desired flow pattern or profile immediately downstream of the outflow side 52) using fluid flow modeling. The baffle member(s) 80' can be incorporated into the stent frame 36 (e.g., during a laser cut process) and optionally shape set at a desired angular orientation (e.g., where the stent frame 36 is formed of a shape memory material such as Nitonol™). Alternatively, the baffle member(s) 80' can be formed apart from the stent frame 36 and attached thereto, such as from a polymer or fabric material. With these and other optional embodiments, the baffle member(s) 80' can be attached (e.g., sewn) to the stent frame 36 during the fabrication process.

Figure 11A:
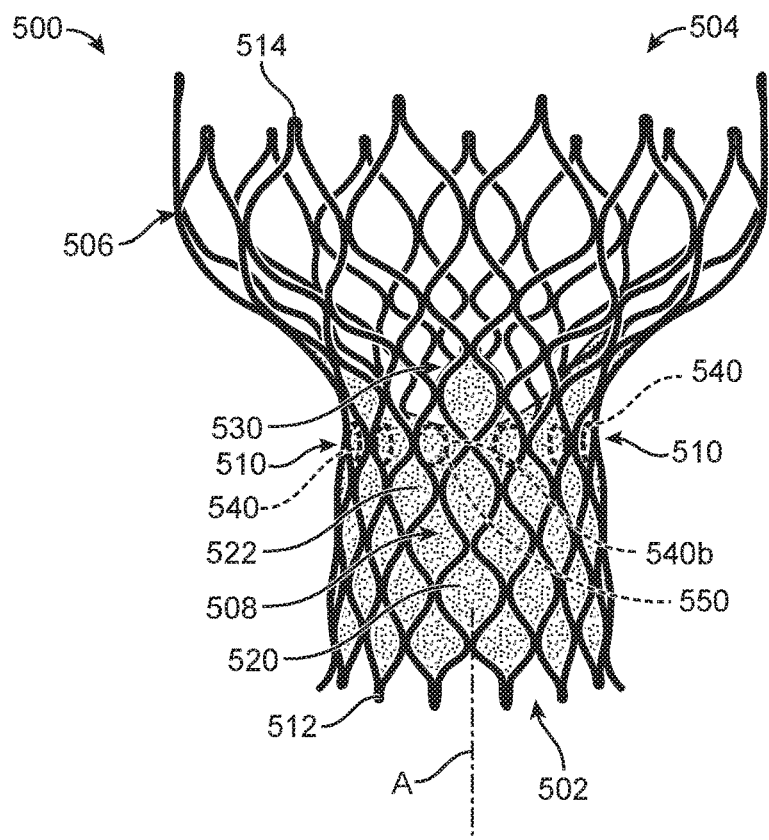
FIG. 11A is a side view of another prosthetic valve in accordance with principles of the present disclosure.
Figure 11B:
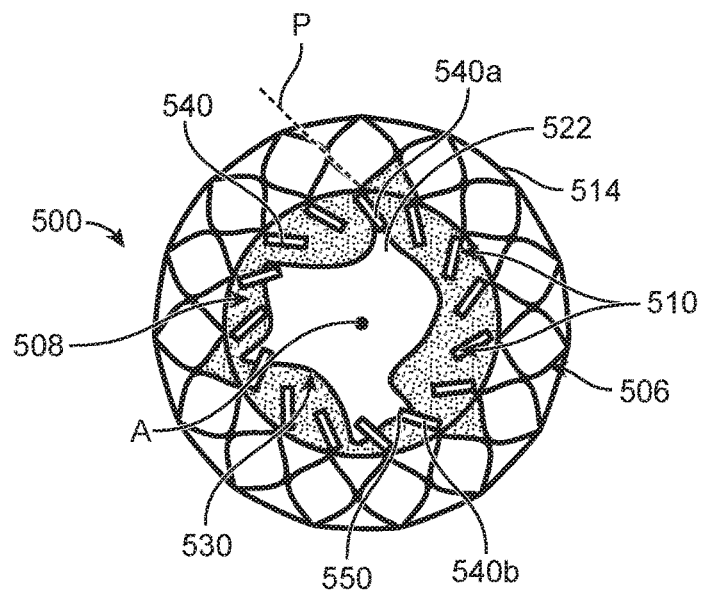
FIG. 11B is a top plan view of the prosthetic valve of FIG. 11A.

With the above descriptions of the laminar flow baffle structure 41 in mind, FIGS. 11A and 11B illustrates another prosthetic valve 500 in accordance with principles of the present disclosure that defines an inflow end 502 opposite an outflow end 504. The prosthetic valve 500 includes a stent frame 506, a valve structure 508 and a laminar flow baffle structure 510 (referenced generally).

The stent frame 506 and the valve structure 508 can have any of the configurations described elsewhere in this disclosure, and are in no way limited to the constructions possibly implicated by the views of FIGS. 11A and 11B. For example, a shape of the stent frame 506 in the normal, expanded condition can be appropriate for deployment at a native aortic valve anatomy, mitral valve anatomy, or alternatively, would be shaped in accordance with any other internal anatomy of the human body. Regardless, the stent frame 506 generally defines a lumen, an inflow margin 512 and an outflow margin 514 opposite the inflow margin 512. In the exemplary embodiment of FIGS. 11A and 11B, the stent frame inflow and outflow margins 512, 514 serve as or define the inflow and outflow ends 502, 504, respectively, of the prosthetic valve 500. The valve structure 508 is disposed within the stent frame lumen, and is configured to provide an inflow side 520 (referenced generally) and an outflow side 522 (referenced generally) opposite the inflow side 520. An outflow track 530 (referenced generally) is established within the lumen downstream of the outflow side 522 and along which fluid flow from the valve structure 504 progresses following implant.

The laminar flow baffle structure 510 is connected to the stent frame 506 and optionally projects into the outflow track 530. With the exemplary embodiment of FIGS. 11A and 11B, the laminar flow baffle structure 510 includes a plurality of baffle members 540 disposed about an inner circumference of the stent frame 506. In other embodiments, a single one of the baffle members 540 is provided. The baffle members 540 can have any of the forms described above (e.g., solid plate or paddle, perforated paddle, rigid material, flexible material, etc.), and are sized, shaped and spatially oriented to encourage laminar or nearly laminar flow into the flow profile of blood as it exits the outflow side 522 of the valve structure 508. For example, the baffle members 540 can be equidistantly disposed about a circumference of the stent frame 506, or can be non-uniformly distributed. In some embodiments, some or all of the baffle members 540 longitudinally aligned (relative to a longitudinal axis A of the stent frame 506); in other embodiments, the baffle members 506 can be arranged to define a spiral-like pattern about the longitudinal axis A. Regardless, one or more of the baffle members 540 project inwardly from the stent frame 506 at an angular orientation relative to the longitudinal axis A as best reflected by FIG. 11B. For example, in some embodiments, a shape of each of the baffle members 540 defines a major plane, such as a major plane P identified for a first baffle member 540a in FIG. 11B. One, some or all of the baffle members 540 are arranged such that the major plane P is off-set from or otherwise does not intersect the longitudinal axis A (e.g., the baffle member(s) 540 does not project from the stent frame 506 in only a radial direction). The angular relationship of each the baffle members 540 relative to the longitudinal axis A can be substantially identical in some embodiments, and is selected to encourage a laminar or nearly laminar flow profile into blood flow exiting the outflow side 522 of the valve structure 508. As the blood flow then progresses along the outflow track 530 and interfaces with the stent frame 506, occurrences of stagnant or turbulent flow at the stent frame 506 and surrounding areas is reduced or eliminated (as compared to a flow profile in the absence of the laminar flow baffle structure 510). Other geometry features can be incorporated into one or more of the baffle members 540 that further encourage or promote a desired flow profile, such as curvature formed at a leading edge 550 (identified for a second baffle member 540b in FIGS. 11A and 11B). The baffle members 540 can be identical or can differ in terms of at least shape or size, and can each optionally extend across at least 5%, and less than 90%, of a diameter of the outflow track 280.

With the exemplary constructions of at least FIGS. 6 and 8-10, the prosthetic heart valve 200 is optionally configured (e.g., sized and shaped) for replacing or repairing a mitral valve. Alternatively, other shapes are also envisioned, adapted to mimic the specific anatomy of the valve to be repaired (e.g., stented prosthetic heart valves useful with the present disclosure can alternatively be shaped and/or sized for replacing a native aortic, pulmonic or tricuspid valve, or useful as an intraluminal valve away from the heart). For example, the prosthetic valves of the present disclosure can be configured for placement in the urinary track (to regulate flow or urine), in the lung (to regulate flow of gas), etc. The baffle structures of the present disclosure can be incorporated into prosthetic valves optionally having one or more additional features as described below.

One or more prosthetic valve embodiments disclosed herein may comprise no support arms, a single support arm, a plurality of support arms, support arms with inner and outer support arm members, variations of structures thereof, and/or one or more pairs of support arms having various structures and attachment points for providing various functions when implanted. It should be understood that the illustrated embodiments hereof are not limited to the number or configuration of support arms illustrated in each figure and that one or more support arms, one or more pairs of support arms and/or the various structures therefore may be substituted across the various embodiments disclosed herein without departing from the scope hereof.

In one or more embodiments, the prosthetic valves of the present disclosure may comprise one or more support arms for engaging one or more native valve leaflets. In one or more embodiments, valve prosthesis may comprise one or more support arms for engaging one or more native chordae. In one or more embodiments, the prosthetic valve may comprise one or more support arms for engaging one or more native valve commissures. In one or more embodiments, the prosthetic valve may comprise one or more support arms for engaging a native valve annulus. In one or more embodiments, prosthetic valve may comprise one or more support arms for engaging one or more native valve tissues or structures. For example, one or more support arms may engage or interact with valve leaflets, chordae, commissures and/or annulus. In one or more embodiments, the prosthetic valve may comprise one or more support arms for engaging one or more heart tissues or structures. In one or more embodiments, the prosthetic valve may comprise one or more support arms for engaging the pulmonary artery. In one or more embodiments, the prosthetic valve may comprise one or more support arms for engaging the aorta.

In one or more embodiments, one or more support arms may be coupled or connected to a central portion, an inflow portion and/or an outflow portion of the prosthetic valve. In one or more embodiments, the prosthetic valve may comprise one or more support arms that may apply one or more forces such as a radial force, an axial force, a lateral force, an inward force, an outward force, an upstream force, and/or a downstream force to one or more valve structures, valve tissues, heart structures and/or heart tissues. In some embodiments, one or more support arms, as described herein, may be considerably longer, shorter, wider, or narrower than shown. In some embodiments, one or more support arms, as described herein, may be narrower at the base, bottom or proximal end portion where the support arms couple to an inflow portion, central portion and/or an outflow portion of the prosthetic valve and wider at the top or distal end portion of the support arm. In some embodiments, one or more support arms, as described herein, may be wider at the base, bottom, or proximal end portion where the support arms couple to the inflow portion, central portion and/or the outflow portion of the prosthetic valve and narrower at the top or distal end portion of the support arm. In some embodiments, one or more support arms, as described herein, may be configured to be a shape and size that can provide a positioning function, valve leaflet capturing function, a stabilization function, an anti-migration function, and/or an anchoring function for valve prosthesis in accordance herewith when the prosthesis is deployed at a native valve site. In some embodiments, one or more support arms, as described herein, may interact, engage, capture, clamp, push against one or more native tissues or structures such as valve leaflets, chordae, annulus, ventricle, and/or atrium. In some embodiments, one or more support arms, as described herein, may comprise a first portion that extends in a forward direction and a second portion that extends in a backward direction. In some embodiments, one or more support arms, as described herein, may comprise a first portion that extends in a backward direction and a second portion that extends in a forward direction. In some embodiments, one or more support arms, as described herein, may comprise one or more portions that may extend horizontally, longitudinally, axially, circumferentially, inward, outward, forward, and/or backward. In some embodiments, one or more support arms, as described herein, may comprise more than one configuration. For example, one or more embodiments of one or more support arms, as described herein, may extend in first direction in a delivery, compressed, and/or collapsed configuration and in a second direction in a deployed or expanded configuration. In one example, a first or delivery direction may be a forward direction and a second or deployed direction may be a backward direction. In another example, a first or delivery direction may be a backward direction and a second or deployed direction may be a forward direction. In one or more embodiments, one or more support arms, as described herein, may comprise a first shape in a delivery configuration and a second shape in a deployed configuration. For example, a first or delivery shape may be a straight shape and a second or deployed shape may be a curved shape.

In some embodiments, one or more support arms, as described herein, may comprise one or more portions that comprise one or more spiral shapes, s-shapes, c-shapes, u-shapes, V-shapes, loop shapes, tine shapes, and/or prong shapes. In some embodiments, one or more support arms, as described herein, may comprise a curved, rounded, and/or flared distal end portion. In some embodiments, one or more support arms, as described herein, may be connected, coupled, attached, and/or extend from one or more locations positioned on the inflow portion, the central portion and/or the outflow portion of the prosthetic valve. For example, in some embodiments, one or more support arms, as described herein, may be connected, coupled, attached, and/or extend from one or more locations positioned on the inflow portion, the central portion and/or the outflow portion of the valve prosthesis stent frame support structure. In some embodiments, one or more support arms, as described herein, may comprise at least a portion that may comprise at least one free end not attached or coupled to the stent frame of the prosthetic valve. In one or more embodiments, one or more support arms and/or one or more of components of a support arm may comprise one or more fixation elements or members such as anchors, barbs, prongs, clips, grommets, sutures, and/or screws. In one or more embodiments, one or more support arms and/or one or more of components of a support arm may comprise, for example, one or more active and/or passive fixation elements or members.

In one or more embodiments, the prosthetic valve may comprise an inflow portion, a central portion, and an outflow portion. In one or more embodiments, the prosthetic valve may comprise a single unitary structure or the prosthetic valve may comprise one or more components or portions coupled or connected together. In one or more embodiments, the prosthetic valve may comprise a central portion comprising a valve body, member, or component. In one or more embodiments, the valve body, structure, member, or component may comprise one or more valve leaflets. In one or more embodiments in accordance herewith, the valve leaflets of the valve body, structure, member, or component are attached to an upstream end of the central portion to extend into an inflow portion of the frame, such that the valve body, structure, member, or component is not solely located on or within the outflow portion of the frame. In one or more embodiments, valve member and/or one or more of its components may comprise one or more materials, as described herein.

In one or more embodiments, the central portion of the prosthetic valve and/or one or more of its components may comprise one or more longitudinal or cross-sectional shapes, such as a geometric shape, a non-geometric shape, a tubular shape, a cylindrical shape, a circular shape, an elliptical shape, an oval shape, a triangular shape, a rectangular shape, a hexagonal shape, a square shape, an hourglass shape, a polygonal shape, a funnel shape, a nozzle shape, a D-shape, a saddle shape, a planar shape, a non-planar shape, a simple geometric shape, and/or a complex geometric shape. In one or more embodiments, the central portion and/or one or more of its components may comprise one or more fixation elements or members such as anchors, barbs, clips, prongs, grommets, sutures, and/or screws. In one or more embodiments, the central portion and/or one or more of its components may comprise a frame, a framework, or stent-like structure, as described herein. In one or more embodiments, the outflow portion and/or one or more of its components may comprise, be covered with, be coated with, or be attached or coupled to one or more materials, as described herein. In one or more embodiments, the central portion and/or one or more of its components may comprise one or more support arms, components, or members as described herein. In one or more embodiments, one or more support arms may comprise one or more cantilever components or portions. In one or more embodiments, the central portion and/or one or more of its components, such as one or more support arms, may be designed to engage and/or push against the native valve annulus. In one or more embodiments, the central portion and/or one or more of its components, such as one or more support arms, may be designed to engage, capture, clamp, hold, and/or trap one or more native valve leaflets. In one or more embodiments, the central portion and/or one or more of its components, such as one or more support arms, may be designed to engage, capture, clamp, hold, and/or trap one or more native chordae. In one or more embodiments, one or more support arms may create or exert a tension force to native chordae. In one or more embodiments, the central portion and/or one or more of its components, such as one or more support arms, may be designed to engage and/or push against one or more native valve commissures.

In one or more embodiments, the prosthetic valve may comprise an inflow, inlet, upstream, or proximal portion connected, coupled, positioned, and/or located at a proximal end or proximal end portion of the central portion of the valve prosthesis. In one or more embodiments, the inflow portion and/or one or more of its components may contact, engage, fixate, capture, clamp, pierce, hold, position, and/or seal the prosthetic valve to one or more heart structures and/or tissues such as atrial tissue, ventricle tissue, valve tissue, annulus tissue, the floor of an atrium, and/or the floor of a ventricle. For example, the inflow portion and/or one or more of its components may engage atrial tissue if the prosthetic valve is positioned in a native mitral valve whereas the inflow portion and/or one or more of its components may engage ventricle tissue if the valve prosthesis is positioned in a native aortic valve. In one or more embodiments, the inflow portion and/or one or more of its components may exert one or more forces, for example, radial and/or axial forces, to one or more heart structures and/or heart tissues. In one or more embodiments, the inflow portion and/or one or more of its components may comprise one or more fixation elements or members such as anchors, barbs, clips, prongs, grommets, sutures, and/or screws. In one or more embodiments, the inflow portion and/or one or more of its components may comprise one or more longitudinal or cross-sectional shapes, such as a geometric shape, a non-geometric shape, a tubular shape, a cylindrical shape, a circular shape, an elliptical shape, an oval shape, a triangular shape, a rectangular shape, a hexagonal shape, a square shape, a polygonal shape, a funnel shape, a nozzle shape, a D-shape, an S-shape, a saddle shape, a simple geometric shape, and/or a complex geometric shape. In one or more embodiments, the inflow portion and/or one or more of its components may be designed to deform to the shape of the native anatomy when the prosthetic valve is implanted. For example, the inflow portion may deform from a pre-delivery circular shape to a post-delivery D-shape following the delivery of the prosthetic valve to a native mitral valve. In one or more embodiments, the inflow portion and/or one or more of its components may comprise a frame, a framework, or stent-like structure, as described herein. In one or more embodiments, the inflow portion and/or one or more of its components may comprise, be covered with, be coated with, or be attached or coupled to one or more materials, as described herein. In one or more embodiments, the inflow portion and/or one or more of its components may comprise one or more support arms, components, or members as described herein. In one or more embodiments, one or more support arms may comprise one or more cantilever components or portions. In one or more embodiments, the inflow portion and/or one or more of its components, such as one or more support arms, may be designed to engage and/or push against the native valve annulus. In one or more embodiments, the inflow portion and/or one or more of its components, such as one or more support arms, may be designed to engage, capture, clamp, hold, and/or trap one or more native valve leaflets. In one or more embodiments, the inflow portion and/or one or more of its components, such as one or more support arms, may be designed to engage, capture, clamp, hold, and/or trap one or more native chordae. In one or more embodiments, one or more support arms may create or exert a tension force to native chordae. In one or more embodiments, the inflow portion and/or one or more of its components, such as one or more support arms, may be designed to engage and/or push against one or more native valve commissures.

In one or more embodiments, the prosthetic valve may comprise an outflow, outlet, downstream, or distal portion connected, coupled, positioned, and/or located at a distal end or distal end portion of the central portion of the prosthetic valve. In one or more embodiments, the outflow portion and/or one or more of its components may contact, engage, fixate, capture, clamp, pierce, hold, position, and/or seal the valve prosthesis to one or more heart structures and/or tissues such as atrial tissue, ventricle tissue, valve tissue, valve leaflet tissue, annulus tissue, and/or chordae tissue. For example, the outflow portion and/or one or more of its components may engage leaflet tissue, chordae tissue, and/or ventricle tissue if the valve prosthesis is positioned in a native mitral valve whereas the outflow portion and/or one or more of its components may engage leaflet tissue and/or aortic tissue if the valve prosthesis is positioned in a native aortic valve. In one or more embodiments, the outflow portion and/or one or more of its components may exert one or more forces, for example, radial and/or axial forces, to one or more heart structures and/or heart tissues. In one or more embodiments, the outflow portion and/or one or more of its components may comprise one or more fixation elements or members such as anchors, barbs, prongs, clips, grommets, sutures, and/or screws. In one or more embodiments, the outflow portion and/or one or more of its components may comprise one or more longitudinal or cross-sectional shapes, such as a geometric shape, a non-geometric shape, a tubular shape, a cylindrical shape, a circular shape, an elliptical shape, an oval shape, a triangular shape, a rectangular shape, a hexagonal shape, a square shape, a polygonal shape, a funnel shape, a nozzle shape, a D-shape, an S-shape, a saddle shape, a simple geometric shape, and/or a complex geometric shape. In one or more embodiments, the outflow portion and/or one or more of its components may be designed to deform to the shape of the native anatomy when the prosthetic valve is implanted. For example, the outflow portion may deform from a pre-delivery circular shape to a post-delivery D-shape following the delivery of the prosthetic valve to a native mitral valve. In one or more embodiments, the outflow portion and/or one or more of its components may comprise a frame, a framework, or stent-like structure, as described herein. In one or more embodiments, the outflow portion and/or one or more of its components may comprise, be covered with, be coated with, or be attached or coupled to one or more materials, as described herein. In one or more embodiments, the outflow portion and/or one or more of its components may comprise one or more support arms, components, or members as described herein. In one or more embodiments, the outflow portion and/or one or more of its components, such as one or more support arms, may be designed to engage, capture, clamp, hold, and/or trap one or more native valve leaflets. In one or more embodiments, the outflow portion and/or one or more of its components, such as one or more support arms, may be designed to engage, capture, clamp, hold, and/or trap one or more native chordae. In one or more embodiments, one or more support arms may create or exert a tension force to native chordae. In one or more embodiments, the outflow portion and/or one or more of its components, such as one or more support arms, may be designed to engage and/or push against one or more native valve commissures. In one or more embodiments, the outflow portion and/or one or more of its components, such as one or more support arms, may be designed to engage and/or push against the native valve annulus. In one or more embodiments, one or more support arms may comprise one or more cantilever components or portions.

In one or more embodiments, the prosthetic valve and/or one or more of its components or portions may comprise, be covered with, be coated with, or be attached or coupled to one or more biocompatible materials or biomaterials, for example, titanium, titanium alloys, Nitinol, TiNi alloys, shape memory alloys, super elastic alloys, aluminum oxide, platinum, platinum alloys, stainless steels, stainless steel alloys, MP35N, elgiloy, haynes 25, stellite, pyrolytic carbon, silver carbon, glassy carbon, polymers or plastics such as polyamides, polycarbonates, polyethers, polyesters, polyolefins including polyethylenes or polypropylenes, polystyrenes, polyurethanes, polyvinylchlorides, polyvinylpyrrolidones, silicone elastomers, fluoropolymers, polyacrylates, polyisoprenes, polytetrafluoroethylene, polyethylene terephthalates, fabrics such as woven fabrics, nonwoven fabrics, porous fabrics, semi-porous fabrics, nonporous fabrics, Dacron fabrics, polytetrafluoroethylene (PTFE) fabrics, polyethylene terephthalate (PET) fabrics, materials that promote tissue ingrowth, rubber, minerals, ceramics, hydroxapatite, epoxies, human or animal protein or tissue such as collagen, laminin, elastin or fibrin, organic materials such as cellulose, or compressed carbon, and/or other materials such as glass, and the like. Materials that are not considered biocompatible may be modified to become biocompatible by a number of methods well known in the art. For example, coating a material with a biocompatible coating may enhance the biocompatibility of that material. Biocompatible materials or biomaterials are usually designed and constructed to be placed in or onto tissue of a patient's body or to contact fluid of a patient's body. Ideally, a biocompatible material or biomaterial will not induce undesirable reactions in the body such as blood clotting, tumor formation, allergic reaction, foreign body reaction (rejection) or inflammatory reaction; will have the physical properties such as strength, elasticity, permeability, and flexibility required to function for the intended purpose; may be purified, fabricated and sterilized easily; will substantially maintain its physical properties and function during the time that it remains in contact with tissues or fluids of the body.

In one or more embodiments, the prosthetic valve and/or one or more of its components or portions may comprise and/or be coupled or attached to one or more graft materials. In accordance with embodiments hereof, the graft material or portions thereof may be a low-porosity woven fabric, such as polyester, DACRON® polyester, or polytetrafluoroethylene (PTFE), which creates a one-way fluid passage when attached to the stent frame of the valve prosthesis. In an embodiment, the graft material or portions thereof may be a looser knit or woven fabric, such as a polyester or PTFE knit, which can be utilized when it is desired to provide a medium for tissue ingrowth and the ability for the fabric to stretch to conform to a curved surface. In another embodiment, polyester velour fabrics may alternatively be used for the graft material or portions thereof, such as when it is desired to provide a medium for tissue ingrowth on one side and a smooth surface on the other side. These and other appropriate cardiovascular fabrics are commercially available from Bard Peripheral Vascular, Inc. of Tempe, Ariz., for example. In another embodiment, the graft material or portions thereof may be a natural material, such as pericardium or another membranous tissue.

In one or more embodiments, the prosthetic valve and/or one or more of its components or portions may comprise, be coated with, be covered with, be constrained by, or be attached or coupled to a shape memory material, a bioresorbable material, and/or a biodegradable material, such as a natural or synthetic biodegradable polymer, non-limiting examples of which include polysaccharides such as alginate, dextran, cellulose, collagen, and chemical derivatives thereof, proteins such as albumin, and copolymer blends thereof, alone or in combination with synthetic polymers, polyhydroxy acids, such as polylactides, polyglycolides and copolymers thereof, poly(ethylene terephthalate), poly(hydroxybutyric acid); poly(hydroxyvaleric acid), poly [lactide-co-(E-caprolactone)]; poly[glycolide-co-(E-caprolactone)], polycarbonates, poly(pseudo amino acids); poly(amino acids); poly(hydroxyalkanoate)s, polyanhydrides; polyorthoesters, and blends and copolymers thereof. In one or more embodiments, one or more surfaces of the valve prosthesis and/or one or more of its components or portions may comprise, be covered with, be coated with, or be attached or coupled to one or more glues and/or adhesives, such as a bioglue or bioadhesive used to help anchor and/or seal the valve prosthesis to native tissue.

In one or more embodiments, one or more surfaces of the prosthetic valve and/or one or more of its components or portions may comprise, be covered with, be coated with, or be attached or coupled to one or more radioactive materials and/or biological agents, for example, an anticoagulant agent, an antithrombotic agent, a clotting agent, a platelet agent, an anti-inflammatory agent, an antibody, an antigen, an immunoglobulin, a defense agent, an enzyme, a hormone, a growth factor, a neurotransmitter, a cytokine, a blood agent, a regulatory agent, a transport agent, a fibrous agent, a protein, a peptide, a proteoglycan, a toxin, an antibiotic agent, an antibacterial agent, an antimicrobial agent, a bacterial agent or component, hyaluronic acid, a polysaccharide, a carbohydrate, a fatty acid, a catalyst, a drug, a vitamin, a DNA segment, a RNA segment, a nucleic acid, a lectin, an antiviral agent, a viral agent or component, a genetic agent, a ligand and/or a dye (which acts as a biological ligand). Biological agents may be found in nature (naturally occurring) or may be chemically synthesized by a variety of methods well known in the art.

In one or more embodiments, the prosthetic valve and/or one or more of its components or portions may comprise, be coated with, be covered with, or be attached or coupled to one or more biological cells or tissues, for example, tissue cells, cardiac cells, contractile cells, muscle cells, heart muscle cells, smooth muscle cells, skeletal muscle cells, autologous cells, allogenic cells, xenogenic cells, stem cells, genetically engineered cells, non-engineered cells, mixtures of cells, precursor cells, immunologically neutral cells, differentiated cells, undifferentiated cells, natural tissue, synthetic tissue, animal tissue, human tissue, porcine tissue, equine tissue, porcine tissue, bovine tissue, ovine tissue, autologous tissue, allogenic tissue, xenogenic tissue, autograft tissue, genetically engineered tissue, non-engineered tissue, mixtures of tissues, cardiac tissue, pericardial tissue, cardiac valve tissue, membranous tissue, and/or intestinal submucosa tissue. In one or more embodiments, valve prosthesis and/or one or more of its components or portions may comprise, be covered with, be coated with, or be attached or coupled to one or more materials that promote the growth of cells and/or tissue. In one or more embodiments, the cell and/or tissue promoting materials may comprise, possess or be configured to possess physical characteristics such as size, shape, porosity, matrix structure, fiber structure, and/or chemical characteristics such as growth factors, biological agents, that promote and/or aid, for example, in the adherence, proliferation and/or growth of desired cells and/or tissues in vivo following implantation or ex vivo prior to implantation. In one or more embodiments, the cell and/or tissue promoting materials may accelerate the healing response of the patient following the implantation of the valve prosthesis. In one or more embodiments, the cell and/or tissue promoting materials may comprise pockets, parachutes, voids, and/or openings, for example, that may trap cells and/or tissues and/or promote cells and/or tissues to proliferate, grow and/or heal.

In one or more embodiments, the prosthetic valve may comprise one or more active and/or passive fixation elements or members such as anchors, barbs, prongs, clips, grommets, sutures, and/or screws. In one or more embodiments, one or more active and/or passive fixation elements or members may be delivered separately from the prosthetic valve. In one or more embodiments, one or more active and/or passive fixation elements or members may be delivered before, during, and/or after the prosthetic valve implant procedure. In one or more embodiments, one or more active fixation elements or members may be activated by pushing, pulling, twisting, screwing and/or turning motion or movement. In one or more embodiments, one or more fixation elements or members may be released or engaged via an unsheathing, an unsleeving, a dissolving, and/or a degrading action. In one or more embodiments, one or more active and/or passive fixation elements or members may be delivered using a fixation element delivery system. In one or more embodiments, one or more active and/or passive fixation elements or members may be coupled, connected, and/or attached to the prosthetic valve stent or frame. In one or more embodiments, the prosthetic valve stent or frame may comprise a unitary structure that comprises one or more active and/or passive fixation elements. In one or more embodiments, one or more active and/or passive fixation elements may be coupled, connected, and/or attached to the prosthetic valve skirt and/or graft material. In one or more embodiments, one or more fixation elements or members may be designed to increasingly engage one or more heart tissues and/or structures via any movement of the prosthetic valve relative to heart tissue and/or structures during one or more cardiac cycles. For example, a barbed fixation element that further embeds itself into tissue via movement of the prosthetic valve prosthesis relative to tissue in one direction and then resists movement of the prosthetic valve relative to tissue in the opposite direction.

The prosthetic valves of the present disclosure provide a marked improvement over previous designs. By incorporating a baffle structure tailored to induce laminar or near laminar flow into blood flow exiting the outflow side of the valve structure, as the blood flow then interfaces with the stent frame or other regions of the prosthetic valve, occurrences of stagnant or turbulent flow are reduced or eliminated, thereby eliminating a possible contributor to thrombus formation.

Although the present disclosure has been described with reference to preferred embodiments, workers skilled in the art will recognize that changes can be made in form and detail without departing from the spirit and scope of the present disclosure.

What is claimed is:

1. A prosthetic valve having an inflow end opposite an outflow end, the prosthetic valve comprising:
a stent frame defining a lumen;
a valve structure disposed within the lumen and configured to define an inflow side and an outflow side opposite the inflow side;
wherein an outflow track is established within the lumen downstream of the outflow side and along which fluid flow from the valve structure progresses; and
a baffle structure connected to the stent frame downstream of the outflow side; wherein the baffle structure further includes a plurality of baffle members each projecting into the lumen.

2. The prosthetic valve of claim 1, wherein the baffle structure is configured and located to encourage laminar flow into blood flow immediately downstream of the outflow side.

3. The prosthetic valve of claim 1, wherein the baffle structure is configured to manipulate a natural flow profile of blood flow at the outflow side of the valve structure.

4. The prosthetic valve of claim 3, wherein the baffle structure is configured to disrupt at least 10% of the natural flow profile.

5. The prosthetic valve of claim 1, wherein the lumen has a diameter and further wherein the baffle structure includes a first baffle member projecting across less than an entirety of the diameter.

6. The prosthetic valve of claim 1, wherein the plurality of baffle members are located about a circumference of the stent frame.

7. The prosthetic valve of claim 6, wherein the baffle members are equidistantly spaced.

8. The prosthetic valve of claim 6, wherein the baffle members are longitudinally aligned.

9. The prosthetic valve of claim 6, wherein at least one of the baffle members is arranged at an angle relative to a longitudinal axis of the stent frame.

10. The prosthetic valve of claim 6, wherein each of the baffle members terminates in a leading edge opposite the stent frame, and further wherein the leading edge of at least one of the baffle members is curved.

11. The prosthetic valve of claim 6, wherein at least one of the baffle members is a paddle.

12. The prosthetic valve of claim 1, wherein the stent frame defines the outflow end of the prosthetic valve, and further wherein the baffle structure is located between the outflow end of the stent frame and the outflow side of the valve structure.

13. The prosthetic valve of claim 1, wherein the prosthetic valve is a prosthetic heart valve.

14. The prosthetic valve of claim 1, wherein the prosthetic valve is a prosthetic mitral valve.

15. The prosthetic valve of claim 1, wherein at least one baffle member defines a major plane and the stent frame defines a longitudinal axis; further wherein at least one baffle member is arranged such that the major plane does not intersect the longitudinal axis of the stent frame.

16. A method of regulating fluid flow through a body vessel of a patient, the method comprising:
implanting a prosthetic valve within the body vessel, the prosthetic valve having an inflow end opposite an outflow end and including:
a stent frame defining a lumen,
a valve structure disposed within the lumen and configured to define an inflow side and an outflow side opposite the inflow side,
wherein an outflow track is established within the lumen downstream of the outflow side and along which fluid flow from the valve structure progresses,
a baffle structure connected to the stent frame downstream of the outflow side; wherein the baffle structure further includes a plurality of baffle members each projecting into the lumen,
wherein fluid flow within the body vessel is naturally directed to the inflow side;
and further wherein the valve structure functions to alternately allow and occlude fluid flow from the inflow side to the outflow side;
and even further wherein the baffle structure functions to encourage laminar flow into fluid flow from the outflow side.

17. The method of claim 16, wherein fluid flow from the outflow side of the valve structure interfaces with the baffle structure prior to exiting from the outflow end.

18. The method of claim 16, wherein fluid flow from the outflow side of the valve structure interfaces with the baffle structure after exiting from the outflow side, and then interfaces with the stent structure after interfacing with the baffle structure.

19. The method of claim 16, wherein the body vessel includes a native mitral valve annulus.

\* \* \* \* \*